United States Patent
Dees, Jr. et al.

(10) Patent No.: US 10,779,949 B2
(45) Date of Patent: Sep. 22, 2020

(54) ANATOMICAL MOTION HINGED PROSTHESIS

(71) Applicant: Smith & Nephew, Inc., Memphis, TN (US)

(72) Inventors: Roger Ryan Dees, Jr., Senatobia, MS (US); Paul Charles Crabtree, Jr., Nesbit, MS (US); Jonathan Kirk Nielsen, Dana Point, CA (US)

(73) Assignee: Smith & Nephew, Inc., Memphis, TN (US)

( * ) Notice: Subject to any disclaimer, the term of this patent is extended or adjusted under 35 U.S.C. 154(b) by 337 days.

(21) Appl. No.: 15/676,024

(22) Filed: Aug. 14, 2017

(65) Prior Publication Data

US 2018/0008421 A1    Jan. 11, 2018

Related U.S. Application Data

(63) Continuation of application No. 13/964,306, filed on Aug. 12, 2013, now Pat. No. 9,730,799, which is a
(Continued)

(51) Int. Cl.
*A61F 2/38* (2006.01)

(52) U.S. Cl.
CPC .............. *A61F 2/385* (2013.01); *A61F 2/384* (2013.01); *A61F 2/38* (2013.01); *A61F 2/3859* (2013.01)

(58) Field of Classification Search
CPC .............. A61F 2/38; A61F 2/384; A61F 2/385
See application file for complete search history.

(56) References Cited

U.S. PATENT DOCUMENTS

| 3,748,662 A | 7/1973 | Helfet |
| 3,774,244 A | 11/1973 | Walker |

(Continued)

FOREIGN PATENT DOCUMENTS

| CN | 1087506 A | 6/1994 |
| CN | 101484094 A | 7/2009 |

(Continued)

OTHER PUBLICATIONS

Response dated Nov. 5, 2007 In related U.S. Appl. No. 10/499,047.
(Continued)

*Primary Examiner* — Bruce E Snow
*Assistant Examiner* — Melissa A Hoban

(57) ABSTRACT

A hinged knee prosthesis comprises a tibial component and a femoral component. The tibial component is configured to attach to a tibia. The tibial component has a bearing surface. The femoral component is configured to hingedly attach to the tibial component and rotate relative to the tibial component. The femoral component comprises a medial condyle and a lateral condyle. The medial and lateral condyles have an eccentric sagittal curvature surface configured to rotate and translate on the bearing surface of the tibial component. A method of rotating a hinged knee through a range of flexion is provided. The method fixedly attaches a femoral component to a tibial component. Axial rotation of the femoral component is induced relative to the tibial component when the hinged knee is flexed.

19 Claims, 21 Drawing Sheets

Related U.S. Application Data continuation of application No. 12/307,102, filed as application No. PCT/US2007/072611 on Jun. 30, 2007, now Pat. No. 8,523,950.

(60) Provisional application No. 60/806,383, filed on Jun. 30, 2006.

(56) References Cited

U.S. PATENT DOCUMENTS

| | | |
|---|---|---|
| 3,798,679 A | 3/1974 | Ewald |
| 3,816,855 A | 6/1974 | Saleh |
| 3,824,630 A | 7/1974 | Johnston |
| 3,837,009 A | 9/1974 | Walker |
| 3,869,731 A | 3/1975 | Waugh et al. |
| 3,924,277 A | 12/1975 | Freeman et al. |
| 3,934,272 A | 1/1976 | Wearne et al. |
| 3,958,278 A | 5/1976 | Lee et al. |
| 4,016,606 A | 4/1977 | Murray et al. |
| 4,178,641 A | 12/1979 | Grundei et al. |
| 4,207,627 A | 6/1980 | Cloutier |
| 4,209,861 A | 7/1980 | Walker et al. |
| 4,213,209 A | 7/1980 | Insall et al. |
| 4,249,270 A | 2/1981 | Bahler et al. |
| 4,262,368 A | 4/1981 | Lacey |
| 4,301,553 A | 11/1981 | Noiles |
| 4,309,778 A | 1/1982 | Buechel et al. |
| 4,340,978 A | 7/1982 | Buechel et al. |
| 4,353,135 A | 10/1982 | Forte et al. |
| 4,358,859 A | 11/1982 | Schurman et al. |
| 4,462,120 A | 7/1984 | Rambert et al. |
| 4,474,177 A | 10/1984 | Whiteside |
| 4,524,766 A | 6/1985 | Petersen |
| 4,538,305 A | 9/1985 | Engelbrecht et al. |
| 4,568,348 A | 2/1986 | Johnson et al. |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner et al. |
| 4,703,751 A | 11/1987 | Pohl |
| 4,711,639 A | 12/1987 | Grundei |
| 4,714,472 A | 12/1987 | Averill et al. |
| 4,714,473 A | 12/1987 | Bloebaum |
| 4,721,104 A | 1/1988 | Kaufman |
| 4,722,330 A | 2/1988 | Russell et al. |
| 4,731,086 A | 3/1988 | Whiteside et al. |
| 4,770,663 A | 9/1988 | Hanslik et al. |
| 4,787,383 A | 11/1988 | Kenna |
| 4,822,365 A | 4/1989 | Walker et al. |
| 4,834,758 A | 5/1989 | Lane |
| 4,865,606 A | 9/1989 | Rehder |
| 4,926,847 A | 5/1990 | Luckman |
| 4,936,853 A | 6/1990 | Fabian et al. |
| 4,938,769 A | 7/1990 | Shaw |
| 4,944,757 A | 7/1990 | Martinez et al. |
| 4,950,297 A | 8/1990 | Elloy et al. |
| 4,950,298 A | 8/1990 | Gustilo et al. |
| 4,963,152 A | 10/1990 | Hofmann et al. |
| 4,979,949 A | 12/1990 | Matsen, III et al. |
| 5,002,547 A | 3/1991 | Poggie et al. |
| 5,007,933 A | 4/1991 | Sidebotham et al. |
| 5,011,496 A | 4/1991 | Forte et al. |
| 5,021,061 A | 6/1991 | Wevers et al. |
| 5,032,134 A | 7/1991 | Lindwer |
| 5,047,057 A | 9/1991 | Lawes |
| 5,053,037 A | 10/1991 | Lackey |
| 5,062,852 A | 11/1991 | Dorr et al. |
| 5,071,438 A | 12/1991 | Jones et al. |
| 5,080,675 A | 1/1992 | Lawes et al. |
| 5,092,869 A | 3/1992 | Waldron |
| 5,098,436 A | 3/1992 | Ferrante et al. |
| 5,100,409 A | 3/1992 | Coates et al. |
| 5,104,824 A | 4/1992 | Clausen, Jr. et al. |
| 5,107,824 A | 4/1992 | Rogers et al. |
| 5,116,375 A | 5/1992 | Hofmann |
| 5,122,144 A | 6/1992 | Bert et al. |
| 5,129,909 A | 7/1992 | Sutherland |
| 5,133,758 A | 7/1992 | Hollister |
| 5,133,759 A | 7/1992 | Turner |
| 5,147,405 A | 9/1992 | Van Zie et al. |
| 5,147,406 A | 9/1992 | Houston et al. |
| 5,176,710 A | 1/1993 | Hahn et al. |
| 5,181,925 A | 1/1993 | Houston et al. |
| 5,201,881 A | 4/1993 | Evans |
| 5,203,807 A | 4/1993 | Evans et al. |
| 5,219,362 A | 6/1993 | Tuke et al. |
| 5,226,916 A | 7/1993 | Goodfellow et al. |
| 5,228,459 A | 7/1993 | Caspari et al. |
| 5,234,433 A | 8/1993 | Bert et al. |
| 5,236,432 A | 8/1993 | Matsen, III et al. |
| 5,236,461 A | 8/1993 | Forte |
| 5,250,050 A | 10/1993 | Poggie et al. |
| 5,263,498 A | 11/1993 | Caspari et al. |
| 5,282,803 A | 2/1994 | Lackey |
| 5,282,867 A | 2/1994 | Mikhail |
| 5,282,870 A | 2/1994 | Moser et al. |
| 5,304,181 A | 4/1994 | Caspari et al. |
| 5,314,481 A | 5/1994 | Bianco |
| 5,314,482 A | 5/1994 | Goodfellow et al. |
| 5,326,358 A | 7/1994 | Aubriot et al. |
| 5,330,532 A | 7/1994 | Ranawat |
| 5,330,533 A | 7/1994 | Walker |
| 5,330,534 A | 7/1994 | Herrington et al. |
| 5,336,267 A | 8/1994 | Kubein-Meesenburg et al. |
| 5,358,527 A | 10/1994 | Forte |
| 5,358,529 A | 10/1994 | Davidson |
| 5,358,531 A | 10/1994 | Goodfellow et al. |
| 5,370,699 A | 12/1994 | Hood et al. |
| 5,370,701 A | 12/1994 | Finn |
| 5,405,398 A | 4/1995 | Buford, III et al. |
| 5,411,555 A | 5/1995 | Nieder |
| 5,413,604 A | 5/1995 | Hodge |
| 5,413,607 A | 5/1995 | Engelbrecht et al. |
| 5,417,694 A | 5/1995 | Marik et al. |
| 5,454,816 A | 10/1995 | Ashby |
| 5,470,354 A | 11/1995 | Hershberger et al. |
| 5,480,443 A | 1/1996 | Elias |
| 5,480,446 A | 1/1996 | Goodfellow et al. |
| 5,507,820 A | 4/1996 | Pappas |
| 5,514,143 A | 5/1996 | Bonutti et al. |
| 5,520,695 A | 5/1996 | Luckman |
| 5,549,684 A | 8/1996 | Amino et al. |
| 5,549,686 A | 8/1996 | Johnson et al. |
| 5,549,688 A | 8/1996 | Ries et al. |
| 5,549,689 A | 8/1996 | Epstein et al. |
| 5,556,432 A | 9/1996 | Kubein-Meesenburg et al. |
| 5,609,645 A | 3/1997 | Vinciguerra |
| 5,611,802 A | 3/1997 | Samuelson et al. |
| 5,639,279 A | 6/1997 | Burkinshaw et al. |
| 5,658,342 A | 8/1997 | Draganich et al. |
| 5,658,344 A | 8/1997 | Hurlburt |
| 5,667,511 A | 9/1997 | Vendrely |
| 5,681,354 A | 10/1997 | Eckhoff |
| 5,682,886 A | 11/1997 | Delp et al. |
| 5,690,635 A | 11/1997 | Matsen, III et al. |
| 5,690,637 A | 11/1997 | Wen et al. |
| 5,702,458 A | 12/1997 | Burstein et al. |
| 5,702,466 A | 12/1997 | Pappas |
| 5,723,016 A | 3/1998 | Minns et al. |
| 5,728,162 A | 3/1998 | Eckhoff |
| 5,755,801 A | 5/1998 | Walker et al. |
| 5,755,803 A | 5/1998 | Haines et al. |
| 5,755,804 A | 5/1998 | Schmotzer et al. |
| 5,766,257 A | 6/1998 | Goodman et al. |
| 5,776,200 A | 7/1998 | Johnson et al. |
| 5,782,921 A | 7/1998 | Colleran et al. |
| 5,782,925 A | 7/1998 | Collazo et al. |
| 5,800,552 A | 9/1998 | Forte |
| 5,810,827 A | 9/1998 | Haines et al. |
| 5,824,096 A | 10/1998 | Pappas et al. |
| 5,824,100 A | 10/1998 | Kester et al. |
| 5,824,102 A | 10/1998 | Buscayret |
| 5,824,105 A | 10/1998 | Ries et al. |
| 5,871,545 A | 2/1999 | Goodfellow et al. |

(56) References Cited

U.S. PATENT DOCUMENTS

| | | |
|---|---|---|
| 5,871,546 A | 2/1999 | Colleran et al. |
| 5,879,392 A | 3/1999 | McMinn |
| 5,906,643 A | 5/1999 | Walker |
| 5,935,173 A | 8/1999 | Roger et al. |
| 5,954,770 A | 9/1999 | Schmotzer et al. |
| 5,997,577 A | 12/1999 | Herrington et al. |
| 6,019,794 A | 2/2000 | Walker |
| 6,039,764 A | 3/2000 | Pottenger et al. |
| 6,056,779 A | 5/2000 | Noyer et al. |
| 6,059,788 A | 5/2000 | Katz |
| 6,068,658 A | 5/2000 | Insall et al. |
| 6,080,195 A | 6/2000 | Colleran et al. |
| 6,099,570 A | 8/2000 | Livet et al. |
| 6,120,543 A | 9/2000 | Kubein-Meesenburg et al. |
| 6,132,468 A | 10/2000 | Mansmann |
| 6,139,581 A | 10/2000 | Engh et al. |
| 6,143,034 A | 11/2000 | Burrows |
| 6,165,223 A | 12/2000 | Metzger et al. |
| 6,171,340 B1 | 1/2001 | McDowell |
| 6,190,415 B1 | 2/2001 | Cooke et al. |
| 6,197,064 B1 | 3/2001 | Haines et al. |
| 6,203,576 B1 | 3/2001 | Afriat et al. |
| 6,206,926 B1 | 3/2001 | Pappas |
| 6,210,443 B1 | 4/2001 | Marceaux et al. |
| 6,235,060 B1 | 5/2001 | Kubein-Meesenburg et al. |
| 6,264,696 B1 | 7/2001 | Reigner et al. |
| 6,264,697 B1 | 7/2001 | Walker |
| 6,306,172 B1 | 10/2001 | O Neil et al. |
| 6,325,828 B1 | 12/2001 | Dennis et al. |
| 6,361,564 B1 | 3/2002 | Marceaux et al. |
| 6,379,388 B1 | 4/2002 | Ensign et al. |
| 6,406,497 B2 | 6/2002 | Takei |
| 6,413,279 B1 | 7/2002 | Metzger et al. |
| 6,428,577 B1 | 8/2002 | Evans et al. |
| 6,436,145 B1 | 8/2002 | Miller |
| 6,443,991 B1 | 9/2002 | Running |
| 6,475,241 B2 | 11/2002 | Pappas |
| 6,485,519 B2 | 11/2002 | Meyers et al. |
| 6,494,917 B1 | 12/2002 | McKellop et al. |
| 6,500,208 B1 | 12/2002 | Metzger et al. |
| 6,506,215 B1 | 1/2003 | Letot et al. |
| 6,554,838 B2 | 4/2003 | McGovern et al. |
| 6,558,426 B1 | 5/2003 | Masini |
| 6,569,202 B2 | 5/2003 | Whiteside |
| 6,575,980 B1 | 6/2003 | Robie et al. |
| 6,589,283 B1 | 7/2003 | Metzger et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,695,848 B2 | 2/2004 | Haines |
| 6,702,821 B2 | 3/2004 | Bonutti |
| 6,730,128 B2 | 5/2004 | Burstein |
| 6,755,864 B1 | 6/2004 | Brack et al. |
| 6,764,516 B2 | 7/2004 | Pappas |
| 6,770,097 B2 | 8/2004 | Leclercq |
| 6,770,099 B2 | 8/2004 | Andriacchi et al. |
| 6,773,461 B2 | 8/2004 | Meyers et al. |
| 6,811,568 B2 | 11/2004 | Minamikawa |
| 6,827,723 B2 | 12/2004 | Carson |
| 6,846,329 B2 | 1/2005 | McMinn |
| 6,866,683 B2 | 3/2005 | Gerbec et al. |
| 6,866,684 B2 | 3/2005 | Fell et al. |
| 6,887,276 B2 | 5/2005 | Gerbec et al. |
| 6,893,467 B1 | 5/2005 | Bercovy |
| 6,911,044 B2 | 6/2005 | Fell |
| 6,916,234 B2 | 7/2005 | Suwabe |
| 6,916,340 B2 | 7/2005 | Metzger et al. |
| 6,984,249 B2 | 1/2006 | Keller |
| 6,986,791 B1 | 1/2006 | Metzger |
| 7,018,418 B2 | 3/2006 | Amrich et al. |
| 7,048,741 B2 | 5/2006 | Swanson |
| 7,077,867 B1 | 7/2006 | Pope et al. |
| 7,104,996 B2 | 9/2006 | Bonutti |
| 7,141,053 B2 | 11/2006 | Rosa et al. |
| 7,153,327 B1 | 12/2006 | Metzger |
| 7,160,330 B2 | 1/2007 | Axelson, Jr. et al. |
| 7,297,165 B1 | 11/2007 | Kriek |
| 7,326,252 B2 | 2/2008 | Otto et al. |
| 7,371,240 B2 | 5/2008 | Pinczewski et al. |
| 7,572,292 B2 | 8/2009 | Crabtree et al. |
| 7,625,407 B2 | 12/2009 | Akizuki et al. |
| 7,658,767 B2 | 2/2010 | Wyss |
| 7,871,442 B2 | 1/2011 | Servidio |
| 2001/0001121 A1 | 5/2001 | Lombardo et al. |
| 2001/0018615 A1 | 8/2001 | Biegun et al. |
| 2001/0043918 A1 | 11/2001 | Masini et al. |
| 2002/0032450 A1 | 3/2002 | Trudeau et al. |
| 2002/0055784 A1 | 5/2002 | Burstein et al. |
| 2002/0058997 A1 | 5/2002 | O Connor et al. |
| 2002/0103541 A1 | 8/2002 | Meyers et al. |
| 2002/0107576 A1 | 8/2002 | Meyers et al. |
| 2002/0120340 A1 | 8/2002 | Metzger et al. |
| 2002/0161447 A1 | 10/2002 | Salehi et al. |
| 2002/0173852 A1 | 11/2002 | Felt et al. |
| 2002/0177852 A1 | 11/2002 | Chervitz et al. |
| 2002/0177853 A1 | 11/2002 | Chervitz et al. |
| 2003/0009228 A1 | 1/2003 | Meyers et al. |
| 2003/0009230 A1 | 1/2003 | Gundlapalli et al. |
| 2003/0028196 A1 | 2/2003 | Bonutti |
| 2003/0055494 A1 | 3/2003 | Bezuidenhout et al. |
| 2003/0055501 A1 | 3/2003 | Fell et al. |
| 2003/0055509 A1 | 3/2003 | McCue et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0069591 A1 | 4/2003 | Carson et al. |
| 2003/0093156 A1 | 5/2003 | Metzger et al. |
| 2003/0100953 A1 | 5/2003 | Rosa et al. |
| 2003/0130665 A1 | 7/2003 | Pinczewski et al. |
| 2003/0153977 A1 | 8/2003 | Suguro et al. |
| 2003/0153978 A1 | 8/2003 | Whiteside |
| 2003/0153979 A1 | 8/2003 | Hughes et al. |
| 2003/0163201 A1 | 8/2003 | McMinn |
| 2003/0220697 A1 | 11/2003 | Justin et al. |
| 2003/0225410 A1 | 12/2003 | Chervitz et al. |
| 2003/0225458 A1 | 12/2003 | Donkers et al. |
| 2004/0006393 A1 | 1/2004 | Burkinshaw |
| 2004/0030387 A1 | 2/2004 | Landry et al. |
| 2004/0034432 A1 | 2/2004 | Hughes et al. |
| 2004/0044414 A1 | 3/2004 | Nowakowski |
| 2004/0102852 A1 | 5/2004 | Johnson et al. |
| 2004/0122522 A1 | 6/2004 | Kubein-Meesenburg et al. |
| 2004/0143339 A1 | 7/2004 | Axelson, Jr. et al. |
| 2004/0153066 A1 | 8/2004 | Coon et al. |
| 2004/0153164 A1 | 8/2004 | Sanford et al. |
| 2004/0162620 A1 | 8/2004 | Wyss |
| 2004/0186584 A1 | 9/2004 | Keller |
| 2004/0193280 A1 | 9/2004 | Webster et al. |
| 2004/0199249 A1 | 10/2004 | Fell |
| 2004/0199250 A1 | 10/2004 | Fell |
| 2004/0204766 A1 | 10/2004 | Siebel |
| 2004/0249467 A1 | 12/2004 | Meyers et al. |
| 2004/0249468 A1 | 12/2004 | Suguro et al. |
| 2004/0267363 A1 | 12/2004 | Fell et al. |
| 2005/0021147 A1 | 1/2005 | Tarabichi |
| 2005/0033424 A1 | 2/2005 | Fell |
| 2005/0055102 A1 | 3/2005 | Tornier |
| 2005/0107886 A1* | 5/2005 | Crabtree .............. A61F 2/3854 623/20.24 |
| 2005/0125069 A1 | 6/2005 | Naegerl et al. |
| 2005/0143832 A1 | 6/2005 | Carson |
| 2005/0171604 A1 | 8/2005 | Michalow |
| 2005/0197710 A1 | 9/2005 | Naegerl |
| 2005/0209701 A1 | 9/2005 | Suguro et al. |
| 2005/0246028 A1 | 11/2005 | Pappas et al. |
| 2005/0267363 A1 | 12/2005 | Duchon et al. |
| 2005/0267476 A1 | 12/2005 | Chervitz et al. |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |

(56) References Cited

U.S. PATENT DOCUMENTS

| | | |
|---|---|---|
| 2006/0030855 A1 | 2/2006 | Haines |
| 2006/0030944 A1 | 2/2006 | Haines |
| 2006/0052875 A1 | 3/2006 | Bernero et al. |
| 2006/0058882 A1 | 3/2006 | Haines |
| 2007/0078517 A1 | 4/2007 | Engh et al. |
| 2008/0119940 A1 | 5/2008 | Otto et al. |
| 2008/0154270 A1 | 6/2008 | Haines et al. |
| 2008/0161918 A1 | 7/2008 | Fankhauser et al. |
| 2008/0167722 A1 | 7/2008 | Metzger et al. |
| 2009/0076514 A1 | 3/2009 | Haines |
| 2009/0088860 A1 | 4/2009 | Romeis et al. |
| 2009/0125114 A1 | 5/2009 | May et al. |
| 2009/0143866 A1 | 6/2009 | Servidio |
| 2009/0210066 A1 | 8/2009 | Jasty |
| 2009/0319048 A1 | 12/2009 | Shah et al. |
| 2009/0319049 A1 | 12/2009 | Shah et al. |
| 2010/0016977 A1 | 1/2010 | Masini |
| 2010/0042224 A1 | 2/2010 | Otto et al. |
| 2010/0076567 A1 | 3/2010 | Justin et al. |
| 2010/0100192 A1 | 4/2010 | Haines et al. |
| 2010/0185203 A1 | 7/2010 | Haines |
| 2011/0082559 A1 | 4/2011 | Hartdegen et al. |
| 2011/0125280 A1 | 5/2011 | Otto et al. |
| 2011/0125281 A1 | 5/2011 | Otto et al. |
| 2011/0125282 A1 | 5/2011 | Otto et al. |
| 2011/0125283 A1 | 5/2011 | Otto et al. |
| 2011/0130841 A1 | 6/2011 | Otto et al. |
| 2011/0130842 A1 | 6/2011 | Otto et al. |
| 2011/0130843 A1 | 6/2011 | Otto et al. |
| 2011/0137426 A1 | 6/2011 | Otto et al. |
| 2011/0137427 A1 | 6/2011 | Otto et al. |
| 2011/0137619 A1 | 6/2011 | Otto et al. |

FOREIGN PATENT DOCUMENTS

| | | |
|---|---|---|
| DE | 3022668 A | 12/1981 |
| DE | 3314038 A | 10/1983 |
| DE | 4102509 A | 7/1992 |
| DE | 19529824 A | 2/1997 |
| DE | 19915053 A | 10/1999 |
| DE | 10012059 A | 9/2001 |
| DE | 102005015598 A | 9/2006 |
| EP | 69683 A | 1/1983 |
| EP | 121142 A | 10/1984 |
| EP | 189253 A | 7/1986 |
| EP | 194326 A | 9/1986 |
| EP | 243109 A | 10/1987 |
| EP | 327249 A | 8/1989 |
| EP | 336774 A | 10/1989 |
| EP | 380451 A | 8/1990 |
| EP | 381352 A | 8/1990 |
| EP | 420460 A | 4/1991 |
| EP | 466659 A | 1/1992 |
| EP | 472475 A | 2/1992 |
| EP | 472975 A | 3/1992 |
| EP | 510299 A | 10/1992 |
| EP | 538153 A | 4/1993 |
| EP | 553585 A | 8/1993 |
| EP | 555003 A | 8/1993 |
| EP | 653194 A | 5/1995 |
| EP | 716839 A | 6/1996 |
| EP | 724868 A | 8/1996 |
| EP | 791338 A | 8/1997 |
| EP | 806920 A | 11/1997 |
| EP | 916321 A | 5/1999 |
| EP | 923916 A | 6/1999 |
| EP | 925766 A | 6/1999 |
| EP | 941719 A | 9/1999 |
| EP | 970667 A | 1/2000 |
| EP | 988840 A | 3/2000 |
| EP | 1038286 A | 9/2000 |
| EP | 1285638 A | 2/2003 |
| EP | 1447060 A | 8/2004 |
| EP | 1477143 A | 11/2004 |
| EP | 1721584 A | 11/2006 |
| EP | 1721585 A | 11/2006 |
| EP | 2213262 A | 8/2010 |
| FR | 2508793 A1 | 1/1983 |
| FR | 2635675 A1 | 3/1990 |
| FR | 2664157 A1 | 1/1992 |
| FR | 2701387 A1 | 8/1994 |
| FR | 2710258 A1 | 3/1995 |
| FR | 2710835 A1 | 4/1995 |
| FR | 2760352 A1 | 9/1998 |
| FR | 2776919 A1 | 10/1999 |
| GB | 296443 A | 10/1929 |
| GB | 1363018 A1 | 8/1974 |
| GB | 1409150 A1 | 10/1975 |
| GB | 2007980 A1 | 5/1979 |
| GB | 2296443 A1 | 1/1997 |
| GB | 2324249 A1 | 10/1998 |
| GB | 2335145 A1 | 9/1999 |
| JP | 61170453 A1 | 8/1986 |
| JP | 62133948 A1 | 6/1987 |
| JP | 62254750 A1 | 11/1987 |
| JP | 4297254 A1 | 10/1992 |
| JP | 6237941 A1 | 8/1994 |
| JP | 8500992 A1 | 2/1996 |
| JP | 8224263 A1 | 9/1996 |
| JP | 10501155 A1 | 2/1998 |
| JP | 11504226 A1 | 4/1999 |
| JP | 11313845 A1 | 11/1999 |
| JP | 2000116682 A1 | 4/2000 |
| JP | 2000201955 A1 | 7/2000 |
| JP | 2000312691 A1 | 11/2000 |
| JP | 2001524349 A1 | 12/2001 |
| JP | 2002224149 A1 | 8/2002 |
| JP | 04297254 A1 | 7/2009 |
| JP | 04951797 A1 | 6/2012 |
| RU | 2121319 A1 | 11/1998 |
| WO | WO1991010408 A1 | 7/1991 |
| WO | WO1993003681 A1 | 3/1993 |
| WO | WO1993022990 A1 | 11/1993 |
| WO | WO1993025157 A1 | 12/1993 |
| WO | WO1994005212 A1 | 3/1994 |
| WO | WO1994009730 A1 | 5/1994 |
| WO | WO1994022397 A1 | 10/1994 |
| WO | WO1994028812 A1 | 12/1994 |
| WO | WO1995003003 A1 | 2/1995 |
| WO | WO1995032623 A1 | 12/1995 |
| WO | WO1996001087 A1 | 1/1996 |
| WO | WO1996001588 A1 | 1/1996 |
| WO | WO1996003939 A1 | 2/1996 |
| WO | WO1996023460 A1 | 8/1996 |
| WO | WO1996024311 A1 | 8/1996 |
| WO | WO1997029703 A1 | 8/1997 |
| WO | WO1997029704 A1 | 8/1997 |
| WO | WO1998020817 A1 | 5/1998 |
| WO | WO1999027872 A1 | 6/1999 |
| WO | WO1999030649 A1 | 6/1999 |
| WO | WO2001013825 A1 | 3/2001 |
| WO | WO2003059203 A1 | 7/2003 |
| WO | WO2004100839 A1 | 11/2004 |
| WO | WO2009056836 A1 | 5/2009 |

OTHER PUBLICATIONS

Office Action dated Jan. 24, 2008 in related U.S. Appl. No. 10/499,047.
Response dated Apr. 24, 2008 in related U.S. Appl. No. 10/499,047.
Office Action dated May 13, 2008 In related U.S. Appl. No. 10/499,047.
Response dated Aug. 13, 2008 in related U.S. Appl. No. 10/499,047.
Notice of Allowance dated Oct. 8, 2008 In related U.S. Appl. No. 10/499,047.
International Search Report for International Application No. PCT/US2007/072611, dated Nov. 23, 2007, 4 pages.
First Office Action for Chinese Application No. 20780025036.3, dated Dec. 7, 2010, 8 pages.
Communication Pursuant to Article 94(3) EPC for European Application No. 07799226.1, dated Jul. 8, 2010, 4 pages.
International Search Report for International Application No. PCT/US02/41221, dated Oct. 10, 2003, 3 pages.

(56) References Cited

OTHER PUBLICATIONS

English-Language Translation of EP472475, translated on May 23, 2012, with certification of translation, 11 pages.
Notice of Reasons for Rejection for Japanese Application No. 2009-518598, dated Jun. 26, 2012.
Office Action for U.S. Appl. No. 12/307,102, dated Aug. 9, 2012.
Communication Pursuant to Article 96(2) EPC for European Application No. 02798579.5, dated Mar. 15, 2005.
International Preliminary Report on Patentability for International Application No. PCT/US2007/072611, dated Jan. 6, 2009.
Office Action for Canadian Application No. 2,656,359, dated Nov. 8, 2013.
Patent Examination Report No. 2 for Australian Application No. 2007269203, dated Feb. 12, 2014.
Notice of Reasons for Rejection for Japanese Application No. 2013-096941, dated Apr. 7, 2014.
Office Action in Canadian Application No. 2,656,359, dated Jul. 8, 2014.
Gschwend, N., "GSB Knee Joint," Clinical Orthopaedics and Related Research, No. 132, May 1978, pp. 170-176.
Communication Pursuant to Article 94(3) EPC for European Application No. 07799226.1, dated Aug. 29, 2014.
"S-ROM® Noiles™ Rotating Hinge: Surgical Technique and Reference Guide," © 2002 DePuy Orthopaedics, Inc.
First Office Action for Chinese Application No. 201210471063.6, dated Aug. 29, 2014, with English-language summary.
Second Office Action for Chinese Application No. 201210471063.6, dated Apr. 16, 2015, with English-language summary.
Office Action for Canadian Application No. 2,656,359, dated Nov. 13, 2015.
European Hospital . . . The European Forum For Those in the Business of Making Healthcare Work, 12(5/03):1-24 (Oct./Nov. 2003).
Freeman Samuelson, Total Knee Systems, Biomet, Inc., 1994, attached as Exhibit F, 60 pages.
Freeman, M.A.R., and Samuelson, K.M, Protek® Mark II Total Knee Replacement System, published 1985, 32 pages, attached as Exhibit G.
Protek F/S Modular Total Knee Replacement System, published by Protek, Jan. 1991, pp. 1-58, attached as Exhibit H.
Engh, G.A., et al., "The AMK Total Knee System, Design Rationale and Surgical Procedure," Published by DePuy, 1989, Bates No. DEP00004153-DEP00004201, 50 pages.
Chapman, Michael W., ed., "Primary Total Knee Artluoplasty," Operative Orthopaedics, vol. 1, published by J.B. Lippincott Co., Philadelphia, 1988, pp. 719-725 and p. 86, Bates No. DE000004236-DEP00004247.
Crossett, L.S., et al., "AMK Congruency Instrument System, Surgical Technique," published by DePuy, 1997, Bates No. DEP00004252-DEP00004267, 17 pages.
Engh, G.A., et al., "AMK Surgical Technique," published by DePuy, 1989, Bates No. DEP00004299-DEP00004329, 32 pages.
Desjardins, D., et al., "Interax Total Knee Operative Technique," Interax, 1993, Bates No. DEP00004412-DEP00004432, 22 pages.
Desjardins, D., et al., "Interax Operative Techniques," Interax, 1994, Bates No. DEP00004391-DEP00004411, 22 pages.
Baird, et al., "LCS Uni: Unicompartmental Knee System with Porocoat," published by DePuy, 1991, Bates No. DEP0000452-DEP00004462, 12 pages.
Oxford Meniscal Knee Phase II Unicompartmental Replacement, published by Biomet prior to Jun. 7, 1994, Bates No. DEP00004509-DEP00004515, 8 pages.
Buechel, FF, et al., "Low Contact Stress Meniscal Bearing Unicompartmental Knee Replacement: Long-Term Evaluation of Cemented and Cementless Results," Journal of Orthopaedic Rheumatology, presented at the 57th Annual American Academy of Orthopaedic Surgeons Meeting, New Orleans, LA, Feb. 11, 1990, Bates No. DEP00004096-DEP00004107, 13 pages.
N. J. Unicompartmental Knee, Sep. 15, 1989, Bates No. DEP00004108-DEP00004116, 10 pages.
Buechel, FF, "NJ LCS Unicompartmental Knee System with Porocoat: Surgical Procedure," Oct. 24, 1994, Bates No. DEP00004117-DEP00004130, 15 pages.
Buechel, FF, "NJ LCS Unicompartmental Knee System with Porocoat," 1994, Bates No. DEP00004142-DEP00004152, 11 pages.
Scott, R.D., et al., "P.FC. Signa Uni-compartmental Knee System," published by Johnson & Johnson, 1998, Bates No. DEP00004531-DEP00004539, 10 pages.
Scott, R.D. et al., "Unicondylar Unicompartmental Replacement for Osteoarthritis of the Knee," Journal of Bone and Joint Surgery, vol. 63-A, No. 4, Apr. 1, 1981, pp. 536-544, Bates No. DEP-00004764-DEP00004775.
Uvehammer, J., et al., "In vivo Kinematics of Total Knee Arthroplasty," The Journal of Bone & Joint Suergery (Br), vol. 82-B, No. 4, May 2000, pp. 499-450.
Whiteside Ortholoc Total Knee System: Surgical Procedure, Dow Corning Wright, pp. WMT000001-WMT000040, Jun. 1985.
Zimmer, Insall/Burstein II Constrained Condylar: Modular Knee System, Surgical Technique, copyright 1989.
Exhibits 4. 5 and 8 from *Hudson Surgical Design, Inc.* v. *Zimmer Holdings, Inc.*, Zimmer Inc., Rush System for Health and Rush University Medical Center, Hudson Surgical Design, Inc. 's Opening Brief on Claim Construction Case No. 1 :08-cv-01566, Civil Action No. 08C1566, Document No. 83, filed Nov. 17, 2008, 6 pages.
*Hudson Surgical Design* v. *Zimmer Holdings, Inc., et al.*, Revised Final Claim Construction Chart, filed Mar. 11, 2009, 18 pages.
Haines et al., Accelerated Examination Search Statement and Support Document for Femoral Prosthetic Implant from U.S. Appl. No. 12/638,692, dated Dec. 15, 2009, 85 pages.
Haines et al., Corrected Accelerated Examination Search Statement and Support Document for Femoral Prosthetic Implant from U.S. Appl. No. 12/757,778, dated Apr. 9, 2010, 104 pages.
Advertisement for Protek Mark II PCR Total Knee Replacement System, Journal of Bone and Joint Surgery, vol. 69-B, No. Two (March), 1987, Bates No. DEP00004202-DEP00004230, 29 pages.
Parts Brochure for Mark II Protek, published by Protek, 1987, Bates No. DEP00004231-DEP00004235, 4 pages.
American Academy of Orthopaedic Surgeons, Flyer from the 57th Annual American Academy of Orthopaedic Surgeons Meeting, Feb. 13, 1990, Bates No. DEP00004248-DEP00004267, 4 pages.
Campbell's Operative Orthopaedics, A.H. Crenshaw, ed., 4th Edition, vol. 1, 1963, pp. 29-30, Bates No. DEP00004330-DEP00004333.
"Duraconcept: Design Concepts of the Duracon Total Knee System," published by Howmedica, 1993, Bates No. DEP00004337, 1 page.
Howmedica 1994 Product Catalog, Bates No. DEP00004374-DEP00004375, 2 pages.
Massarella, Antony, "Interax Bulletin No. 6, Tibial Intramedullary Alignment Surgical Techniques," Interax, Feb. 23, 1994, Bates No. DEP00004387-DEP00004390, 4 pages.
New Jersey LCS Total Knee System, FDA PMA-Premarket Approval, 1991, reprinted from http://www.accessdata.fda.gov/scripts/cdrh/cfdocs/cfPMA/pma.cfm?id=3357 on Apr. 8, 2010, Bates No. DEP00004434, 1 page.
Freeman, M.A.R., et al., "Mark II Total Knee Replacement System," published by Protek, 1985, Bates No. DEP00004463-DEP00004492, 30 pages.
Buechel, F.F., "NJ LCS Unicompartmental Knee System with Porocoat," © Biomedical Engineering Trust, South Orange, NJ, 1994, Bates No. DEP00004493-DEP00004503, 11 pages.
Freeman, M.A.R., et al., "F/S Modular Total Knee Replacement System," published by Protek, 1990, Bates No. DEP00004540-DEP00004596, 57 pages.
Broughton, N.S., et al., "Unicompartmental Replacement and High Tibial Osteotomy for Osteoarthritis of the Knee," Journal of Bone and Joint Surgery, vol. 68-B, No. 3, May 1, 1986, pp. 447-452, Bates No. DEP00004752-DEP00004763.
Thornhill, Thomas S., "Unicompartmental Knee Arthroplasty," Clinical Orthopaedics and Related Research, No. 205, Apr. 1, 1986, pp. 121-131, Bates No. DEP00004776-DEP00004791, 16 pages.

(56) References Cited

OTHER PUBLICATIONS

Forst, V.R., et al., "A Special jg for Tibial Resection for the Implantation of GSB-Knee-Prostheses in Problematic Cases," Jun. 1, 1984, pp. 162-166, Bates No. DEP00004838-DEP00004842.

Ingillis, A.E., et al., "Revision Total Knee Replacement," Techniques in Orthopaedics, vol. 5, No. 1, Apr. 1, 1990, pp. 67-73, Bates No. DEP00005583-DEP00005592.

Brochure entitled Aesculap EnduRo Gekoppelte Knieendoprothese Aesculap Orthopaedics B/Braun Sharing Expertise, 8 pages, known prior to Jul. 16, 2010.

Brochure entitled Aesculap EnduRo Gekoppelte Knieendoprothese Operationstechnik Aesculap Orthopaedics B/Braun Sharing Expertise, 56 pages, known prior to Jul. 16, 2010.

Brochure entitled Aesculap EnduRo Rotating Hinge Knee Endoprothesis Manual Surgical Procedure B/Braun Sharing Expertise, 1 page, known prior to Jul. 16, 2010.

Photograph of Aesculap-B Braun EnduRo Knee—rotating hinge (known prior to Jul. 16, 2010).

Office Action dated May 4, 2007 In related U.S. Appl. No. 10/499,047.

Canadian Patent Office, Second Office Action dated Dec. 4, 2017, 4 pages.

\* cited by examiner

ANATOMICAL MOTION HINGED PROSTHESIS

CROSS-REFERENCE TO RELATED APPLICATIONS

This application is a continuation of U.S. patent application Ser. No. 13/964,306, filed Aug. 12, 2013, now allowed, which is a continuation of U.S. patent application Ser. No. 12/307,102, filed Feb. 3, 2010, now U.S. Pat. No. 8,523,950, issued Sep. 3, 2013, which is a U.S. National Phase of International Application No. PCT/US2007/072611, filed Jun. 30, 2007, which claims the benefit of U.S. Provisional Application No. 60/806,383, filed Jun. 30, 2006. Each of the prior applications is incorporated by reference herein in its entirety.

BACKGROUND

1. Field

This application relates generally to knee prostheses and, more particularly, the application relates to hinged knee prostheses.

2. Related Art

Most hinged-knee prostheses only provide a mechanical means to restore the joint in a hinge-like function. Other hinged-knee prostheses provide for more kinematically-correct prostheses; however, they rely mostly on remaining soft tissue to restore normal kinematics to the joint. In most cases, the remaining soft tissue has been compromised and/or missing/removed during surgery. Thus the soft tissue cannot contribute significantly to restoring normal kinematics, particularly anterior/posterior (A/P) translation or normal axial rotation including rotation to the 'screw-home' position. Moreover, the remaining soft tissue may be damaged when restoring normal kinematics by forcing motion of the prostheses.

In prosthetic systems that address axial rotation, current systems address rotation by allowing a rotating platform. Generally, one of the two articulating prostheses (usually the tibial insert or construct) is allowed rotational freedom. This allows the soft tissues to rotate the joint in a more normal fashion. However, most soft tissue has been compromised and cannot reproduce normal or near normal rotation.

A/P translation is a motion that is seldom addressed. In those prostheses that do address A/P translation, a cam mechanism against the joint-linking mechanism (usually a post) or against the tibial articular geometry is used to force the tibia anteriorly relative to the distal femur as the knee flexes. This method of A/P translation is common in a primary total knee arthroplasty (TKA) by the use of a cam and post method in which the cam is on the femoral articulating prosthesis and the post is found on the tibial articulating prosthesis. This is commonly referred to as a posterior or cruciate stabilized knee implant. These hinged knees generally focus forces on a small area (such as a cam with point and/or line contact and post), which may increase wear and decrease the life span of the implant.

In U.S. Pat. Nos. 5,358,527 and 5,800,552, A/P translation is allowed through flexion, yet the hinged knee does not control and/or maintain a constant limit on A/P translation. In other words, the femoral can be flexed and can translate posteriorly when contact to the tibial bearing surface is not maintained. Thus the femoral component does not maintain contact with the tibial component when A/P translation occurs.

There remains a need in the art for kinematically-correct prostheses including A/P translation and/or normal axial rotation. In addition, there remains a need for kinematically-correct prostheses that reduce wear on the prosthesis and reduce forces on the remaining soft tissue.

SUMMARY

The disclosure provides a hinged knee prosthesis comprising a tibial component and a femoral component. The tibial component is configured to attach to a tibia. The tibial component has a bearing surface. The femoral component is configured to hingedly attach to the tibial component and rotate relative to the tibial component. The femoral component comprises a medial condyle and a lateral condyle. The medial and lateral condyles have a sagittal curvature surface configured to induce axial rotation on the bearing surface of the tibial component.

The medial and lateral condyles may have a plurality of eccentric sagittal curvature surfaces configured to rotate on the bearing surface of the tibial component.

The bearing surface of the tibial component is configured with an anterior portion and a posterior portion. The posterior portion of the bearing surface has a portion configured to guide the medial and lateral condyles of the femoral component. Contact points between the femoral component and the tibial component translate in the anterior/posterior direction and rotate axially.

The hinged knee may further comprise an axle hinge pin. The axle hinge pin is located transversely between the medial and lateral condyles. The eccentric sagittal curvature surface has a center of rotation not aligned with the axle hinge pin.

The hinged knee prosthesis may further comprise a post configured to extend from the tibial component to the femoral component. A proximal portion of the post is configured to attach to the axle hinge pin.

The center of rotation of a portion of the eccentric sagittal curvature surface of the medial condyle may not be aligned with the center of rotation of a portion of the eccentric sagittal curvature surface of the lateral condyle. The medial and lateral condyles direct axial rotation of the femoral component relative to the tibial component.

The center of rotation of a portion of the eccentric sagittal curvature surface of the medial condyle may be aligned with the center of rotation of a portion of the eccentric sagittal curvature surface of the lateral condyle, wherein the medial and lateral condyles direct anterior/posterior translation of the femoral component relative to the tibial component.

The medial condyle of the femoral component may further comprise a concentric sagittal curvature surface. The center of rotation of the concentric sagittal curvature surface of the medial condyle is not aligned with the center of rotation of a portion of the eccentric sagittal curvature surface of the lateral condyle. The medial and lateral condyles direct axial rotation of the femoral component relative to the tibial component.

The center of rotation of a first eccentric sagittal curvature surface of the medial condyle may not be aligned with the center of rotation of a first eccentric sagittal curvature surface of the lateral condyle. The medial and lateral condyles direct axial rotation and anterior/posterior translation of the femoral component relative to the tibial component when the first eccentric sagittal curvature surfaces contact the tibial component. The center of rotation of a second eccentric sagittal curvature surface of the medial condyle is aligned with the center of rotation of a second eccentric sagittal curvature surface of the lateral condyle, wherein the medial and lateral condyles direct anterior/posterior translation of the femoral component relative to the tibial component when the second eccentric sagittal curvature surfaces contact the tibial component.

The hinged knee prosthesis may comprise a sleeve configured to receive the post. The sleeve is configured to allow axial rotation of the femoral component relative to the tibial component.

The disclosure provides a method of rotating a hinged knee through a range of flexion. The method fixedly attaches a femoral component to a tibial component. Axial rotation of the femoral component is induced relative to the tibial component when the hinged knee is flexed.

The method may further comprise the step of inducing translation of the femoral component in an anterior/posterior direction relative to the tibial component when the hinged knee is flexed.

The inducing translation step and the inducing axial rotation steps may occur simultaneously.

The inducing axial rotation step may occur through a portion of the range of flexion of the prosthetic knee.

The inducing axial rotation step may occur through a first portion of the range of flexion of the prosthetic knee and a second portion of the range of flexion of the prosthetic knee.

The first portion of the range of flexion may not be adjacent to the second portion of the range of flexion.

The inducing axial rotation step may occur at varying angular velocities as the hinged knee passes through the range of flexion of the knee.

The fixedly attaching step may include connecting a sleeved post to the tibial insert such that a sleeved portion of the sleeved post and a post portion of the sleeved post axially rotate relative to each other. Further the fixedly attaching step may include fixing an axial hinge pin to the sleeved post such that the axial hinge pin transversely connects a medial condyle of the femoral component to the lateral condyle of the femoral component.

The method may further comprise the step of fixing the sleeved portion of the sleeved post to a stem in the tibial component.

The method may further comprise the step of axially displacing the sleeved portion of the sleeved post relative to the post portion of the sleeved post when the hinged knee is flexed.

Thus, kinematically-correct prostheses including A/P translation and/or normal axial rotation may be achieved by the structures in the disclosure. These kinematically-correct prostheses may reduce wear on the prosthesis and reduce forces on the remaining soft tissue. Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments and together with the description, serve to explain the principles of the invention. In the drawings.

DETAILED DESCRIPTION OF THE EMBODIMENTS

Referring to the accompanying drawings in which like reference numbers indicate like elements, FIGS. 1-4 show views of an embodiment of a hinged knee.

Figure 1:
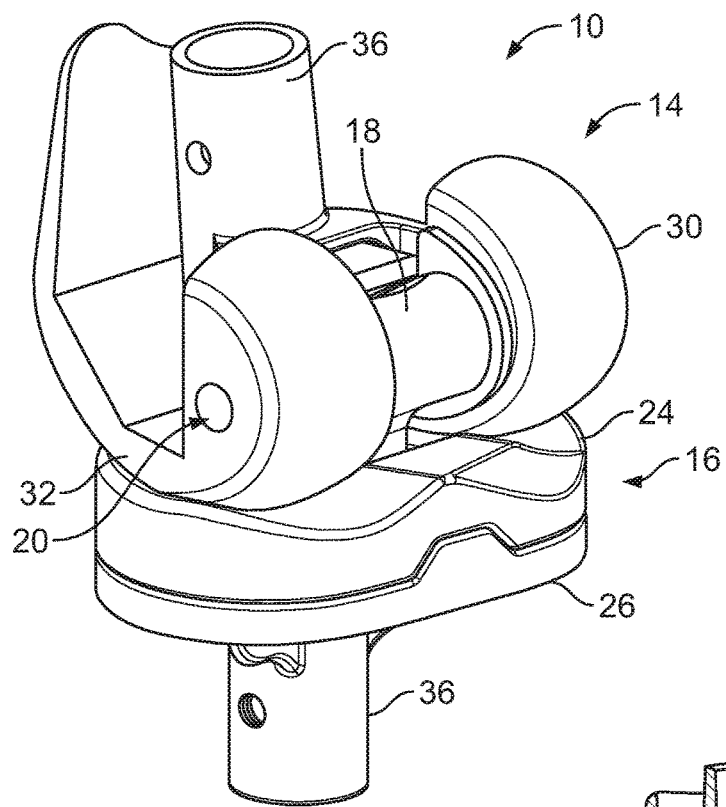
FIG. 1 is an isometric view of an embodiment of a hinged knee.

Turning now to FIG. 1, FIG. 1 is an isometric view of an embodiment of a hinged knee 10. The hinged knee 10 includes a femoral component 14, a tibial component 16, a pin sleeve 18 and a pin 20. The tibial component 16 includes a tibial insert 24 and a tibial base 26. The femoral component 14 includes a medial condyle 30 and a lateral condyle 32. The pin 20 connects the condyles 30 and 32 to the sleeve 18. The sleeve 18 connects to the tibial component through a sleeved post (discussed below).

As the knee flexes, the femoral component 14 rotates relative to the tibial component 16. The femoral component 14 rotates about the pin 20. Axial rotation and anterior/ posterior (A/P) translation of the femoral component 14 is urged by the shape of the tibial insert 24 and the condyles 30 and 32. The axial rotation and anterior/posterior (A/P) translation of the femoral component 14 may occur because the pin 20 is able to axial rotate and be axially translated relative to the post and sleeve of the hinged knee 10.

The femoral component 14 and the tibial component 16 are connected to the femur and tibia, respectively. Stems 36 are inserted into the femur and tibia to fix the femoral component and tibial component to the bones. The length and thickness of these stems may be adjusted based upon required fixation, size of the bones, and size of the intramedullary canals in the bones.

Figure 2:
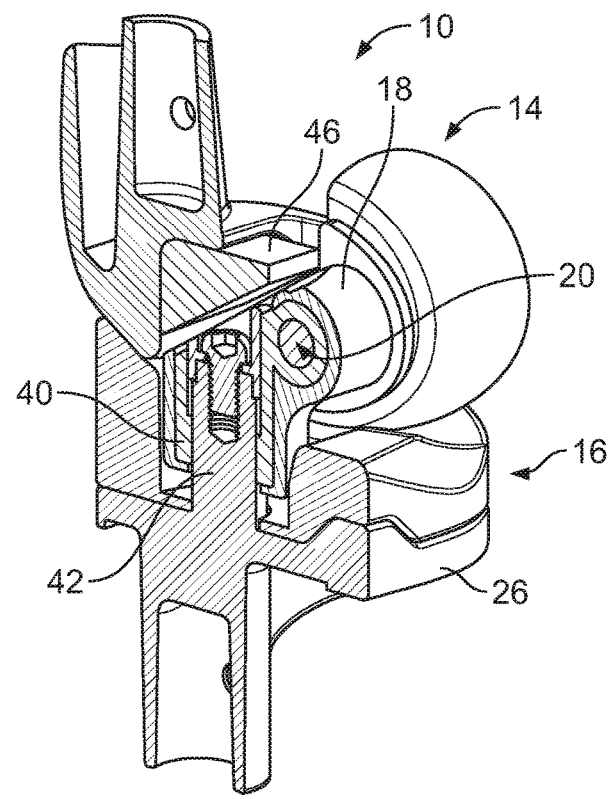
FIG. 2 is a cutaway view of the embodiment of FIG. 1.

Turning now to FIG. 2, FIG. 2 is a cutaway view of the embodiment of FIG. 1. The cutaway is taken in a sagittal plane between the femoral condyles. FIG. 2 shows the pin 20 in the sleeve 18. The sleeve 18 is attached to a post sleeve 40 which surrounds a post 42. The post 42 is attached to the tibial base 26, and may be attached asymmetrically to the tibial base 26. The post sleeve 40 may be axially rotated and axially translated relative to the post 42. The sleeve 18 (and thus the pin 20) may rotate axially and translate axially relative to the tibial component 16. The rotation and translation allow for the femoral component 14 to axially rotate and to translate in the A/P direction. The A/P translation may be accomplished by the condyle surface having a curvature with a center of rotation outside the pin 20. As the femoral component 14 rotates, a bushing 46 stops hyper extension so that the knee may not over extend.

Figure 3:
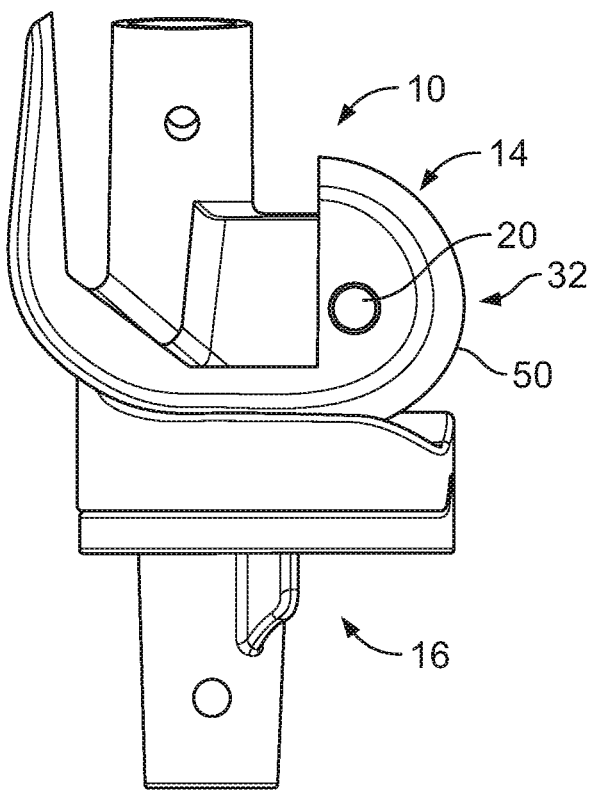
FIG. 3 is a side view of the embodiment of FIG. 1.

Turning now to FIG. 3, FIG. 3 is a side view of the embodiment of FIG. 1. The pin 20 is located posterior to the center of the knee 10. The curve 50 of the condyle 32 is eccentric with respect to the center of rotation of the femoral component 14, which is the pin 20. With respect to the tibial component 16, the pin 20 axially rotates and axially translates as the knee flexes.

Figure 4:
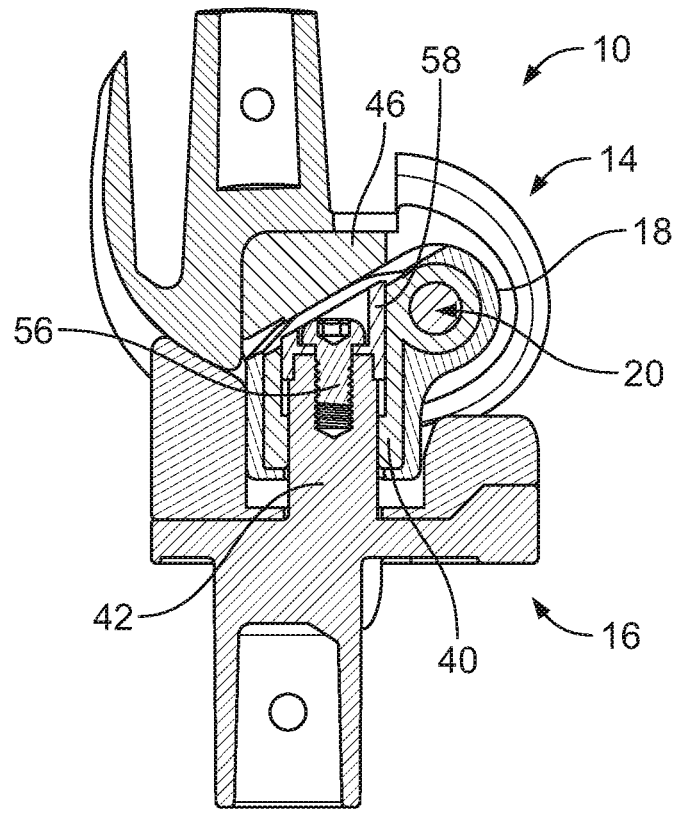
FIG. 4 is a cutaway view of the embodiment of FIG. 3.

Turning now to FIG. 4, FIG. 4 is a cutaway view of the embodiment of FIG. 3. The cutaway is taken along the same sagittal plane of the cutaway in FIG. 2. The cutaway shows the post sleeve 40 and post 42 of the hinged knee 10. A screw 56 fixes a post receiver 58 to the post to lock the post sleeve 40 on the post 42. The post sleeve 40 and pin sleeve 18 then may rotate and translate axially without pulling off the post 42.

Figure 5:
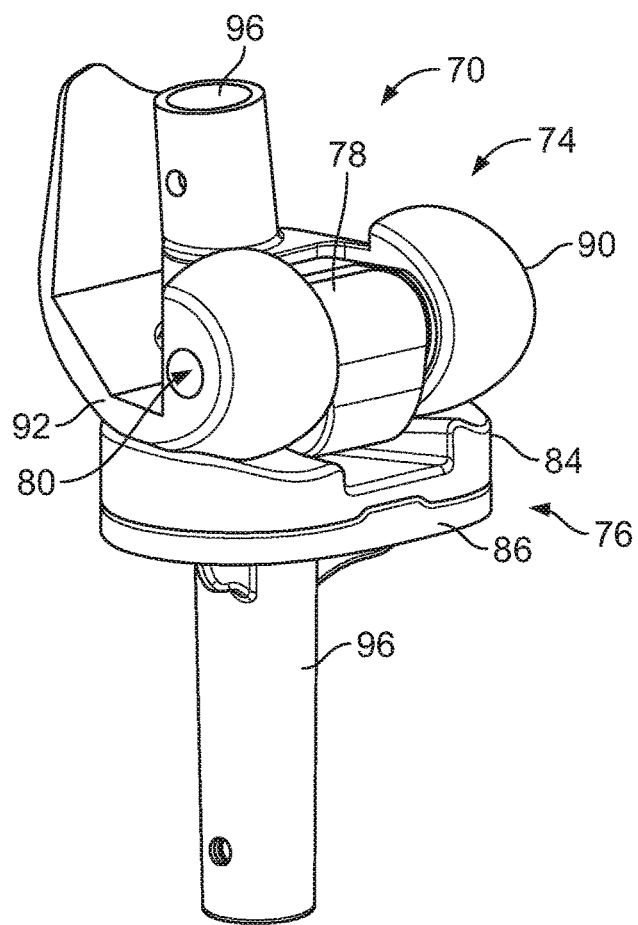
FIG. 5 is an isometric view of an embodiment of a hinged knee.

Turning now to FIGS. 5-8, these FIGs. show views of another embodiment of a hinged knee 70. Turning now to FIG. 5, FIG. 5 is an isometric view of an embodiment of the hinged knee 70. The hinged knee 70 includes a femoral component 74, a tibial component 76, a pin sleeve 78 and a pin 80. The tibial component 76 includes a tibial insert 84 and a tibial base 86. The femoral component 74 includes a medial condyle 90 and a lateral condyle 92. The pin 80 connects the condyles 90 and 92 to the sleeve 78. The sleeve 78 connects to the tibial component through a sleeved post.

As the knee flexes, the femoral component 74 rotates relative to the tibial component 76. The femoral component 74 rotates about the pin 80. Axial rotation and anterior/posterior (A/P) translation of the femoral component 74 is urged by the shape of the tibial insert 84 and the condyles 90 and 92. The axial rotation and anterior/posterior (A/P) translation of the femoral component 74 may occur because the pin 80 is able to axial rotate and be axially translated relative to the post and sleeve of the hinged knee 70.

The femoral component 74 and the tibial component 76 are connected to the femur and tibia, respectively. Stems 96 are inserted into the femur and tibia to fix the femoral component and tibial component to the bones. The length and thickness of these stems may be adjusted based upon required fixation, size of the bones, and size of the intramedullary canals in the bones.

Figure 6:
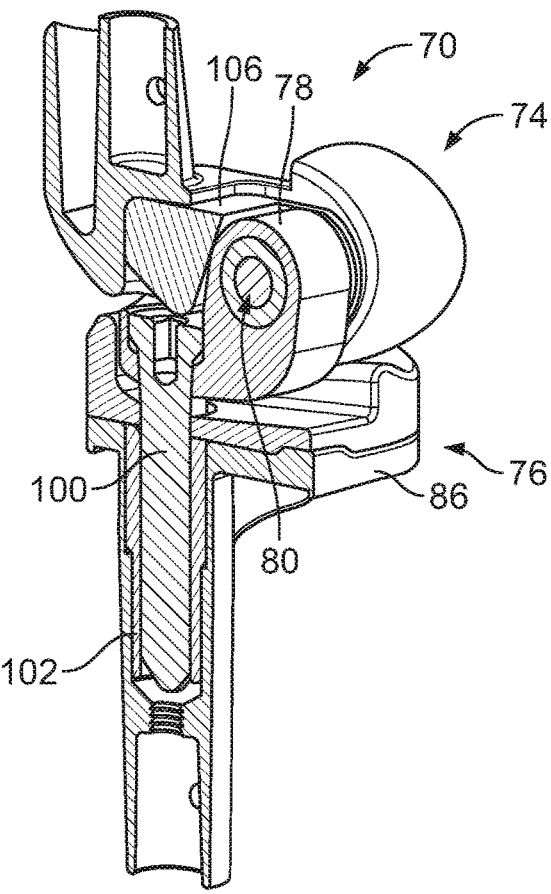
FIG. 6 is a cutaway view of the embodiment of FIG. 5.

Turning now to FIG. 6, FIG. 6 is a cutaway view of the embodiment of FIG. 5. The cutaway is taken in a sagittal plane between the femoral condyles. FIG. 6 shows the pin 80 in the sleeve 78. The sleeve 78 is attached to a post 100 which is inserted into a post sleeve 102. The post sleeve 102 is attached to the tibial base 86. The post 100 may be axially rotated and axially translated relative to the post sleeve 102. The pin sleeve 78 (and thus the pin 80) may rotate axially and translate axially relative to the tibial component 76. The rotation and translation allow for the femoral component 74 to axially rotate and to translate in the A/P direction. The A/P translation may be accomplished by the condyle surface having a curvature with a center of rotation outside the pin 80. As the femoral component 74 rotates, a bushing 106 stops hyper extension so that the knee may not over extend.

Figure 7:
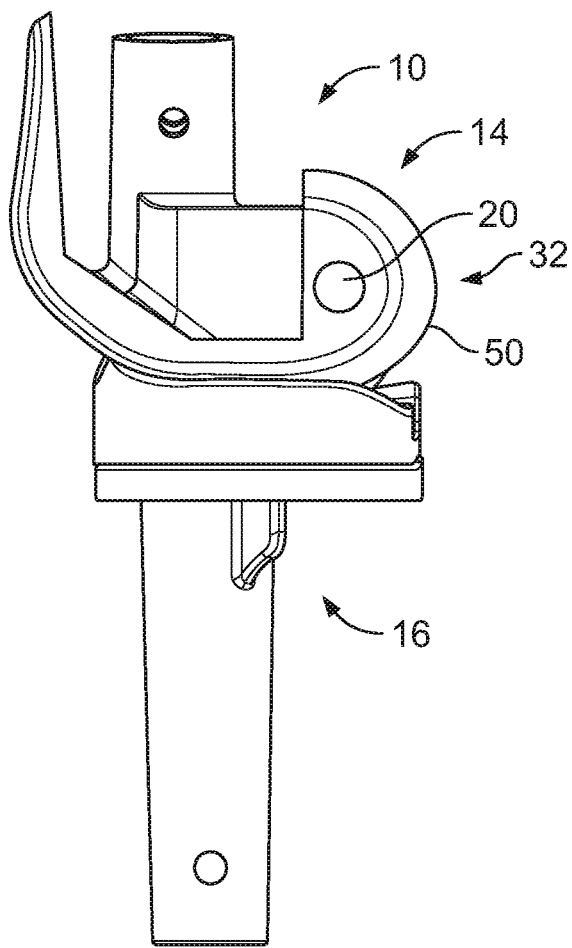
FIG. 7 is a side view of the embodiment of FIG. 5.

Turning now to FIG. 7, FIG. 7 is a side view of the embodiment of FIG. 5. The pin 80 is located posterior to the center of the knee 70. The curve 110 of the condyle 92 is eccentric with respect to the center of rotation of the femoral component 74, which is the pin 80. With respect to the tibial component 76, the pin 80 axially rotates and axially translates as the knee flexes.

Figure 8:
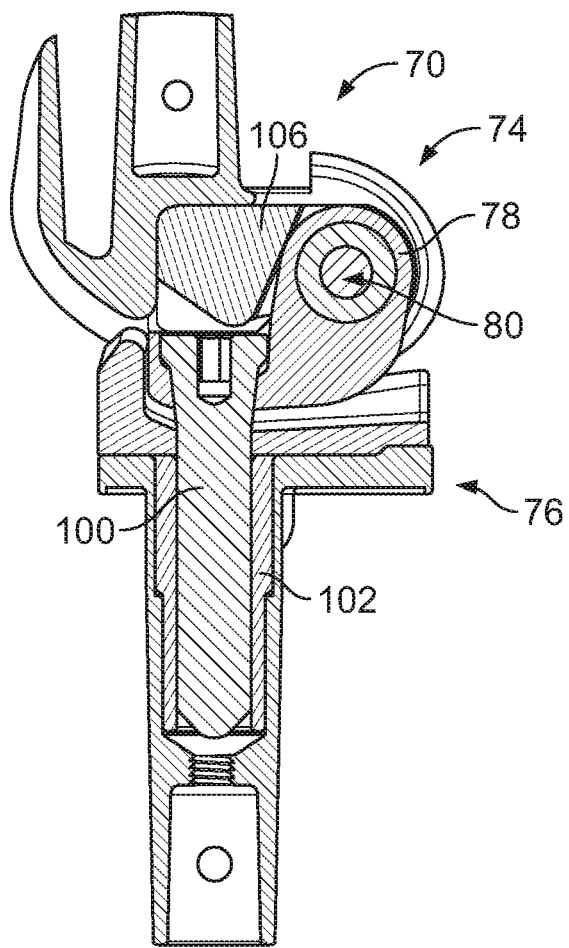
FIG. 8 is a cutaway view of the embodiment of FIG. 7.

Turning now to FIG. 8, FIG. 8 is a cutaway view of the embodiment of FIG. 7. The cutaway is taken along the same sagittal plane of the cutaway in FIG. 6. The cutaway shows the post 100 and post sleeve 102 of the hinged knee 70. An enlarged portion 106 of the post 100 fixes the post 100 to the femoral component 74 so that when the post 100 is inserted in the post sleeve 102, the femoral component 74 is aligned and held in place relative to the tibial component 76. The post 100 and pin sleeve 78 then may rotate and translate axially without pulling the femoral component 74 off the tibial base 76.

Figure 9:
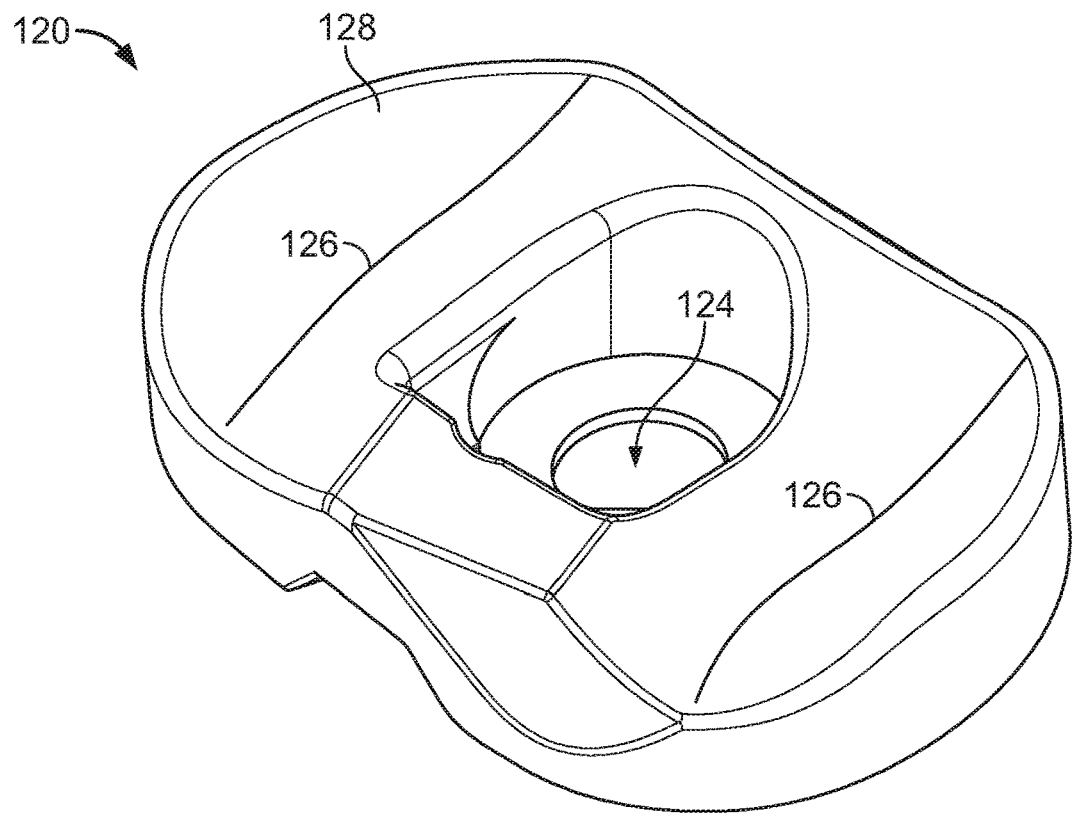
FIG. 9 is an isometric view of an embodiment of a tibial insert.
Figure 10:
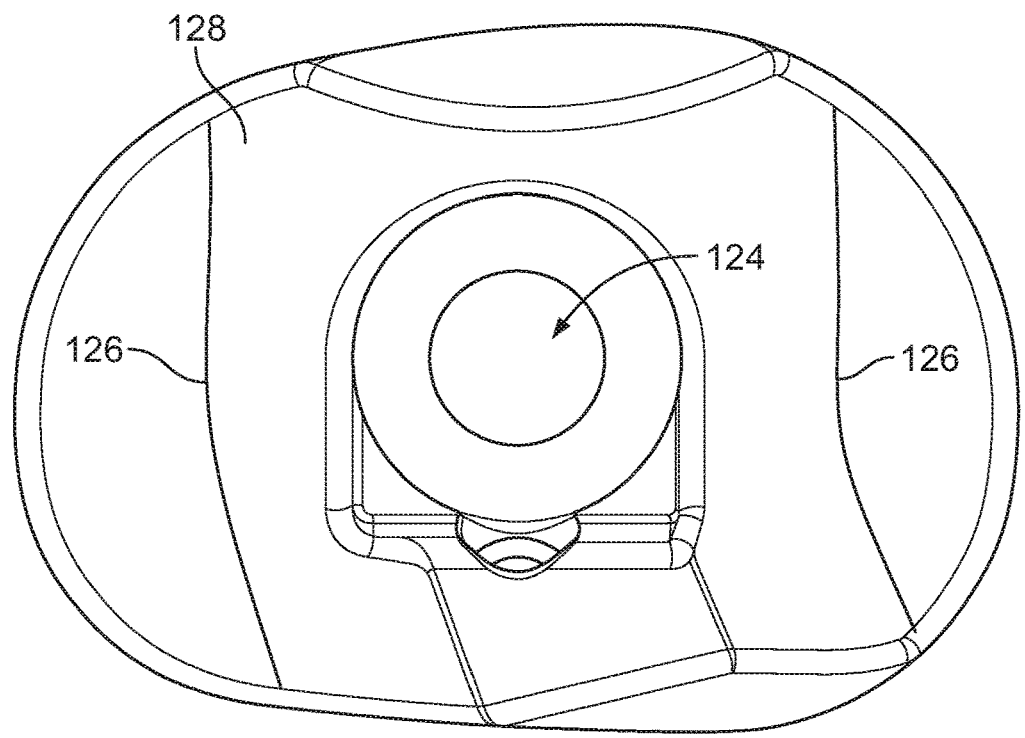
FIG. 10 is a top view of the tibial insert of FIG. 9.

Turning now to FIGS. 9 and 10, these FIGs. show views of a tibial insert 120. FIG. 9 is an isometric view of an embodiment of a tibial insert 120 and FIG. 10 is a top view of the tibial insert 120 of FIG. 9. The tibial insert 120 includes a post hole 124 for receiving the post from either the tibial base or the femoral component. Direction lines 126 on a bearing surface 128 show the lines the femoral component articulates on the tibial insert 120. As the femoral component rotates on the insert 120, the position on the line 126 travels posteriorly. The posterior portion of the tibial insert 120 slopes to axially rotate and translate the femoral component posteriorly. Together in conjunction with the curvature of the condyles, the tibial insert 120 cause A/P translation and axial rotation of the femoral component.

Figure 11:
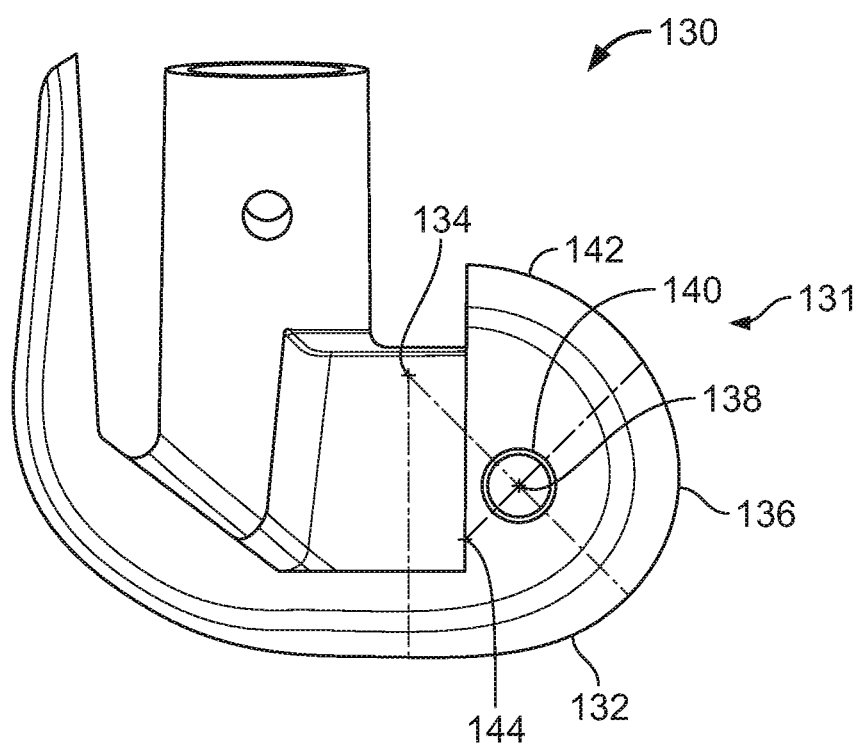
FIG. 11 is a side view of an embodiment of femoral component of a hinged knee.

Turning now to FIG. 11, FIG. 11 is a side view of an embodiment of femoral component 130 of a hinged knee. The curvature of a condyle 131 includes a first distal portion 132 having a first center of rotation 134, a second posterior portion 136 having a second center of rotation 138 concentric with a pin hole 140, and a third proximal portion 142 having a third center of rotation 144. The centers of rotation 134 and 144 are eccentric to the pin hole 140. As the knee rotates, the contact point between the femoral component 130 and the tibial insert produces a force normal to the femoral component 130 and aligned with the center of rotation for that section of the curvature. While the contact point is within the distal portion of the curvature, the normal force points toward the center of rotation 134. At the interface between the distal portion 132 and the posterior portion 136, the normal force is collinear with the centers of rotation 134 and 138. Similarly, at the interface between the posterior portion 136 and the proximal portion 142, the normal force is collinear with the centers of rotation 138 and 144. Thus, the contact points do not jump during rotation but smoothly move.

The eccentricity of the curvatures allows for the lateral forces at the contact points to control axial rotation and A/P translation. Because the forces are normal to the tibial and femoral surfaces, reactive forces at the contact points induce A/P motion and axial rotation. The pins, sleeves, and posts of the hinged knee allow for the translation and rotation of the femoral component 130 with respect to the tibial component.

Figure 12:
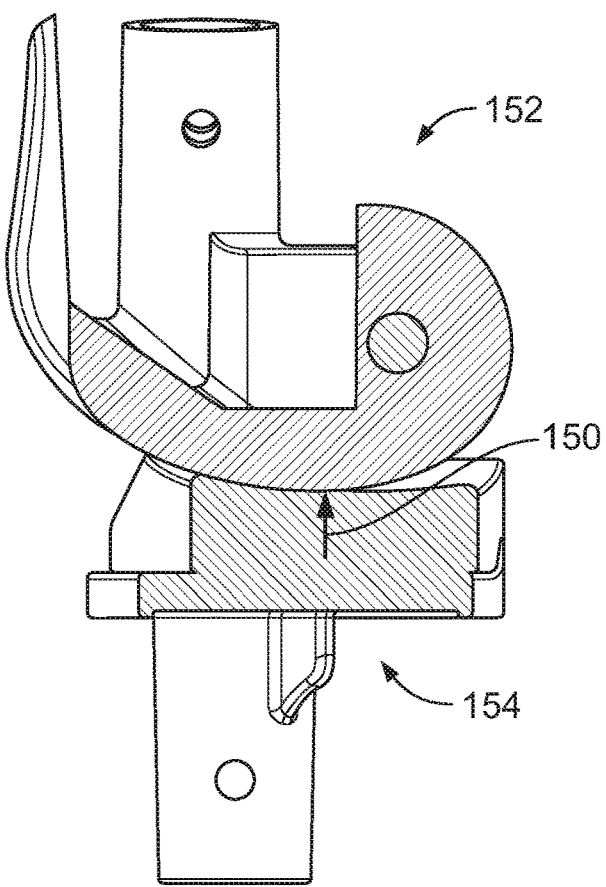
FIGS. 12 and 13 are a side view and an isometric view, respectively, of an embodiment of a hinged knee at extension.
Figure 13:
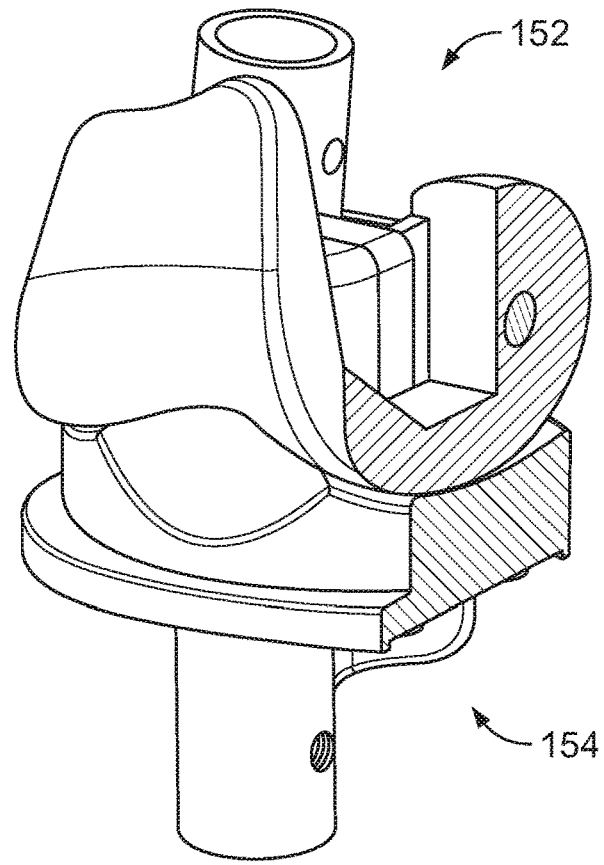

Turning now to FIGS. 12-23, the FIGs. show side views and isometric views of an embodiment of a hinged knee in different angles of flexion. FIGS. 12 and 13 are a side view and an isometric view, respectively, of an embodiment of a hinged knee at extension. A contact point 150 anterior to the pin axis is the contact point between a femoral component 152 and a tibial component 154. The tibial component is posteriorly distal sloped at the contact point 150 so there is a reactive contact force attempting to push the femoral component backwards. FIG. 13 shows the position of the femoral component 152 at extension.

Figure 14:
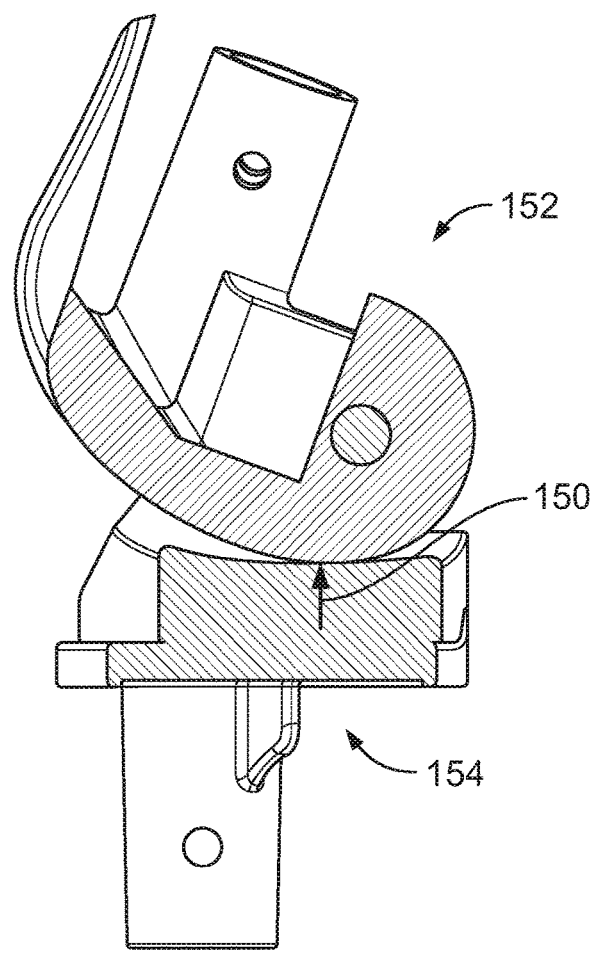
FIGS. 14 and 15 are a side view and an isometric view, respectively, of the hinged knee of FIG. 12 at 20 degrees flexion.
Figure 15:
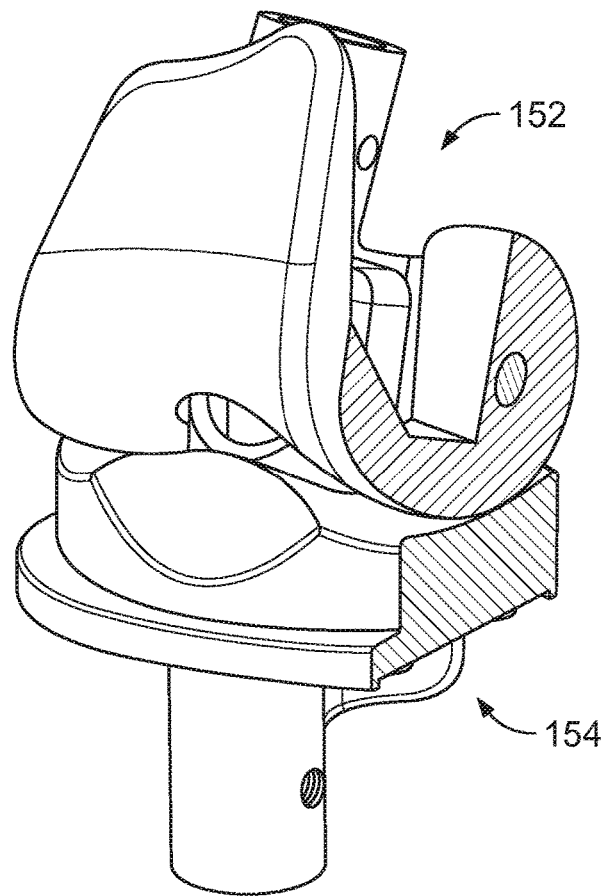

Turning now to FIGS. 14 and 15, FIGS. 14 and 15 are a side view and an isometric view, respectively, of the hinged knee of FIG. 12 at 20 degrees flexion. As the knee flexes, the contact point 150 moves posteriorly. Additionally, as shown in FIG. 15, the femoral component 152 has rotated relative to the tibial component 154. The axial rotation is urged by a differential between the moments created by the reactive forces at the medial and lateral condyles.

Figure 16:
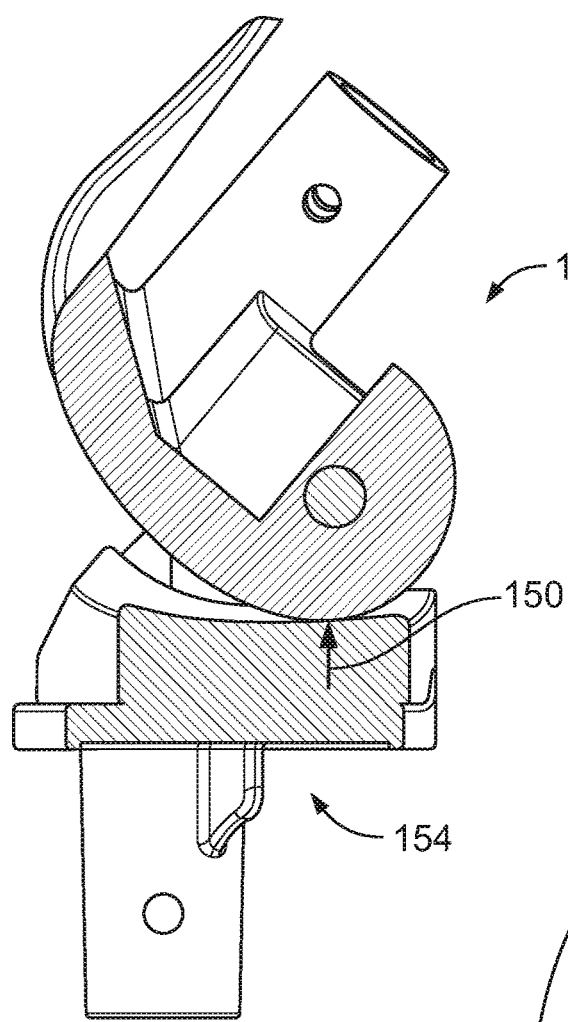
FIGS. 16 and 17 are a side view and an isometric view, respectively, of the hinged knee of FIG. 12 at 40 degrees flexion.
Figure 17:
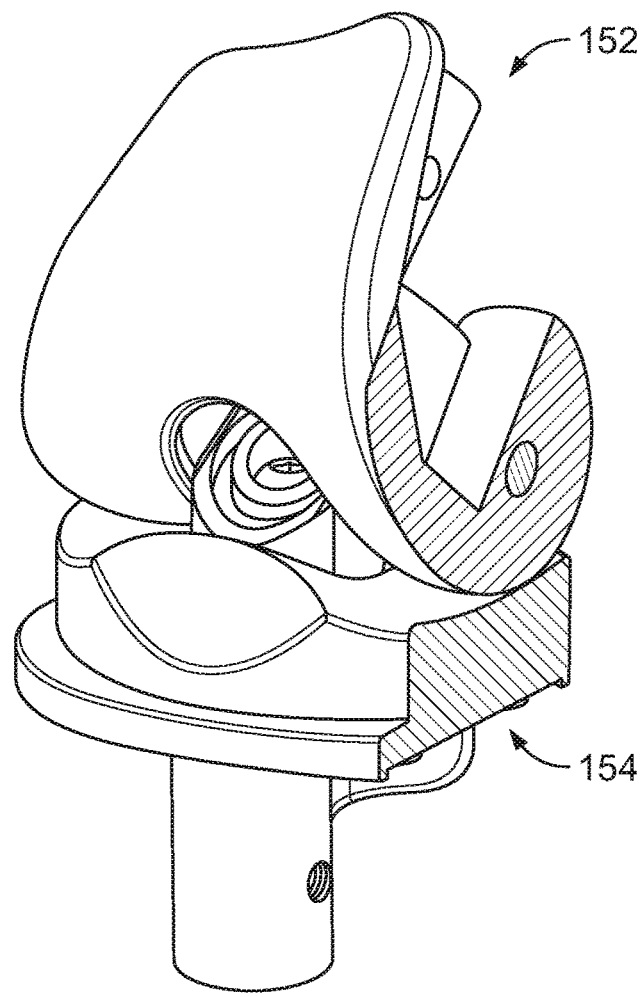

Turning now to FIGS. 16 and 17, FIGS. 16 and 17 are a side view and an isometric view, respectively, of the hinged knee of FIG. 12 at 40 degrees flexion. The contact point 150 has shifted posteriorly and the femoral component has continued to rotate axially. This change in contact point shows the A/P translation of the femoral component as the knee rotates. While most of the motion during early knee flexion is axial rotation, some A/P translation occurs. This "rollback" and rotation is similar to normal joint kinematics. These movements are urged by the shapes of the tibial and femoral component. This minimizes shear forces on the patella which may otherwise try to force these movements of the femoral components. Generation of the shear forces in the patella may cause pain or prosthetic failure.

The contact force 150 is directed through the center of the pin hole as the curvature of the condyle transitions from the distal eccentric portion to the posterior concentric portion discussed with reference to FIG. 11.

Figure 18:
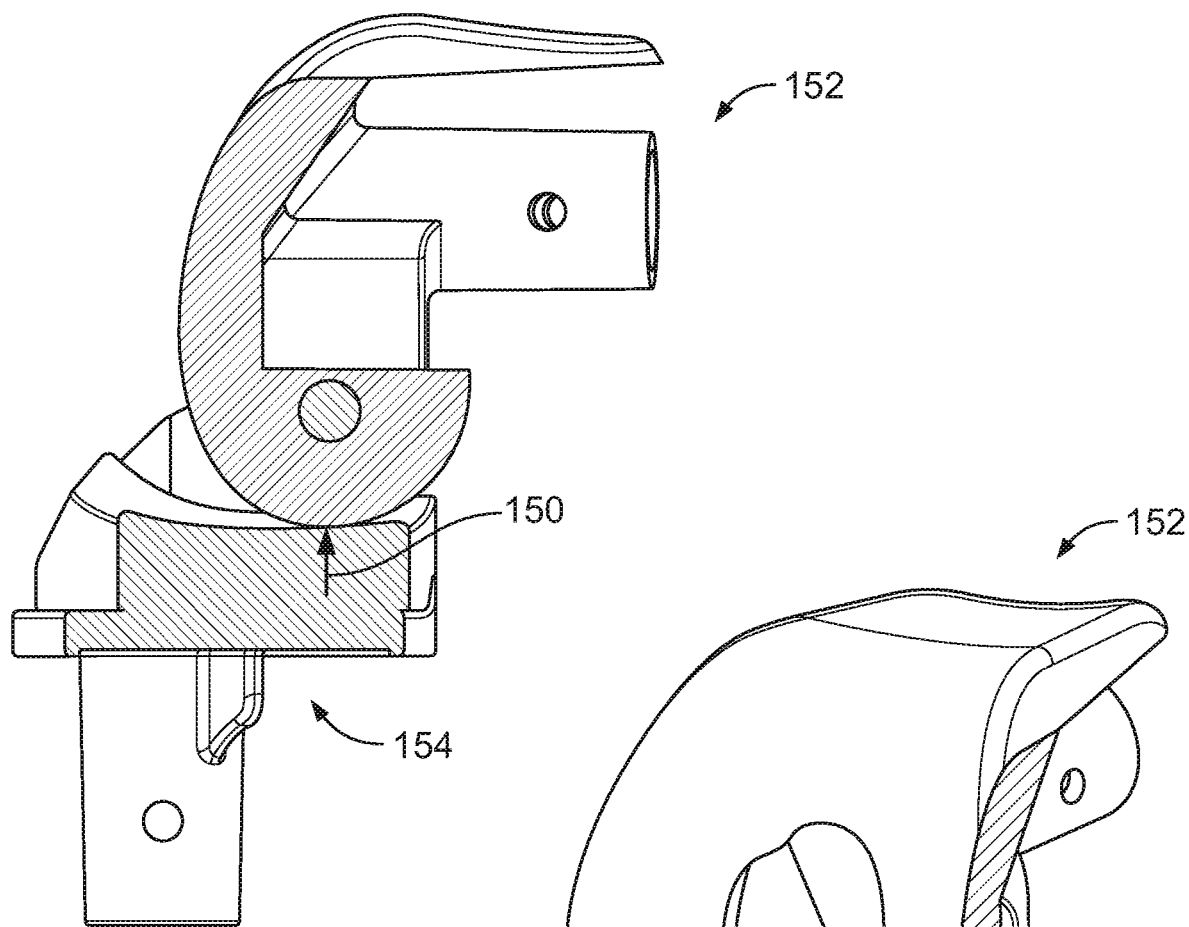
FIGS. 18 and 19 are a side view and an isometric view, respectively, of the hinged knee of FIG. 12 at 90 degrees flexion.
Figure 19:
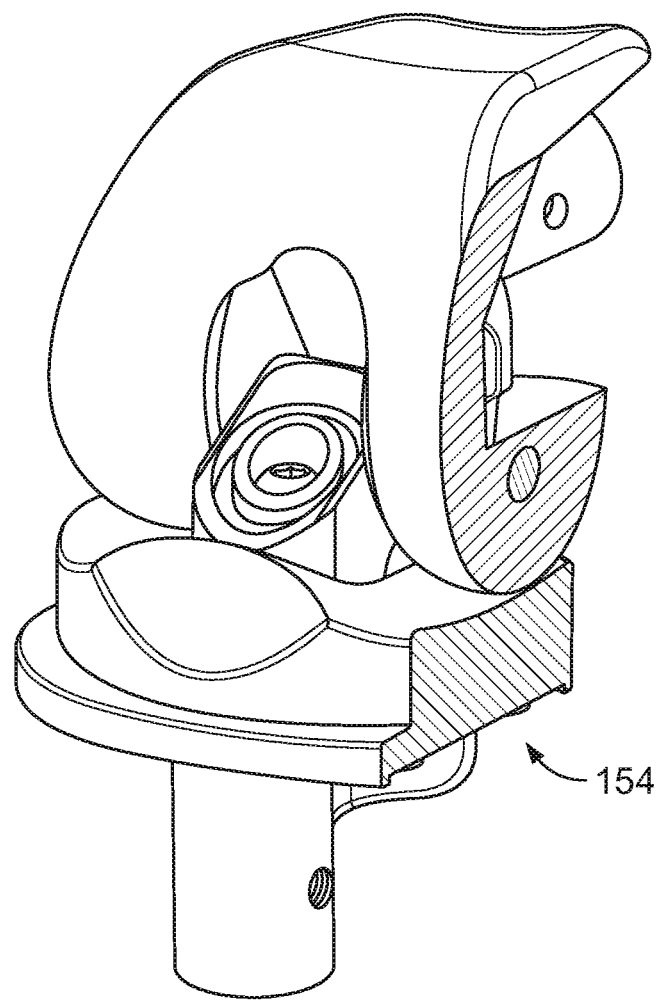

Turning now to FIGS. 18 and 19, FIGS. 18 and 19 are a side view and an isometric view, respectively, of the hinged knee of FIG. 12 at 90 degrees flexion. While flexion continues through the concentric portion, the A/P translation and axial rotation stops. The distance to the center of the pin hole remains constant as the center of curvature for the posterior portion of the condyle is concentric with the pin hole.

Figure 20:
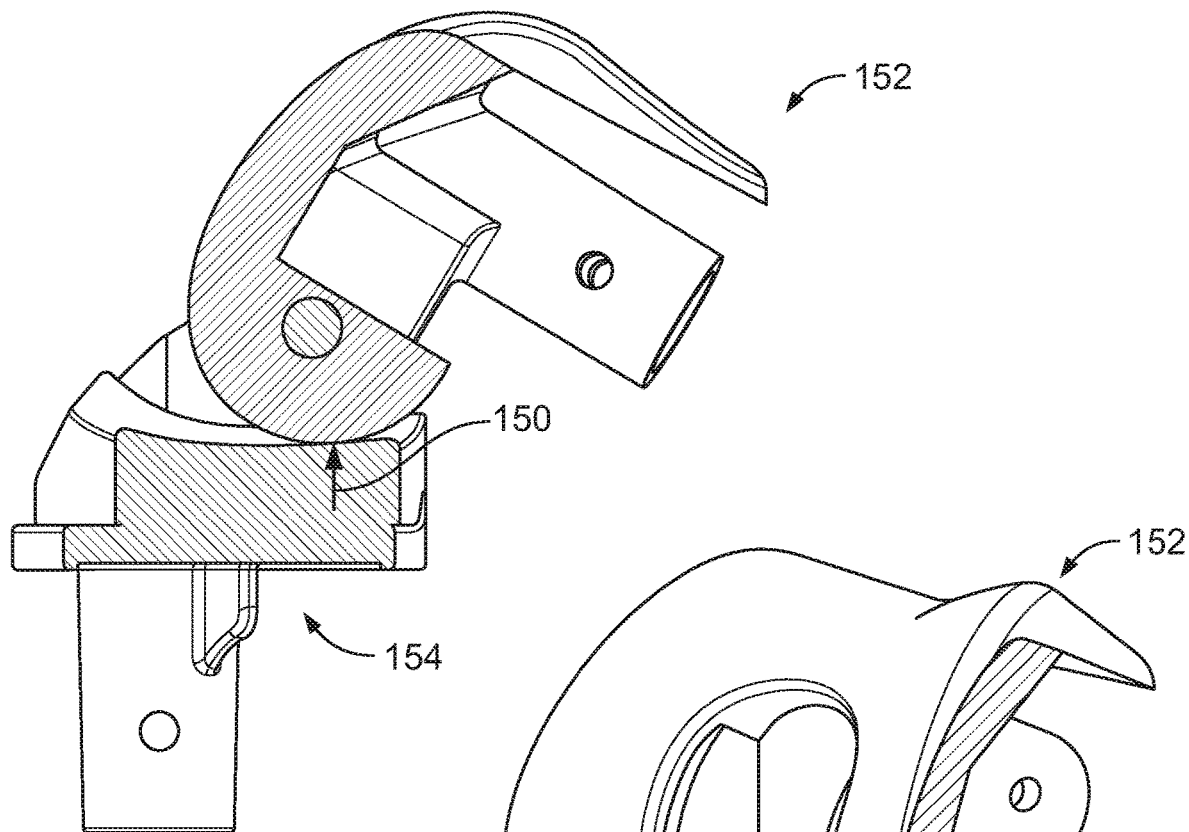
FIGS. 20 and 21 are a side view and an isometric view, respectively, of the hinged knee of FIG. 12 at 120 degrees flexion.
Figure 21:
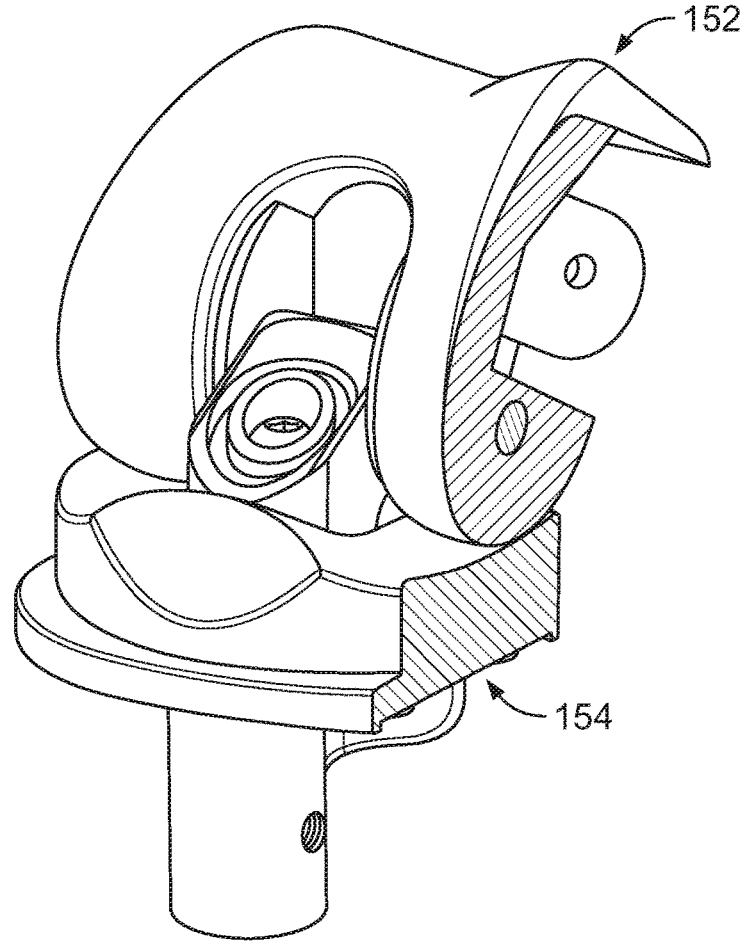

Turning now to FIGS. 20 and 21, FIGS. 20 and 21 are a side view and an isometric view, respectively, of the hinged knee of FIG. 12 at 120 degrees flexion. The contact force 150 is directed through the center of the pin hole as the curvature of the condyle transitions from the posterior concentric portion of the curvature to the proximal eccentric portion discussed with reference to FIG. 11. As the contact force 150 moves posterior the center of the pin hole, the distance from the contact point to the center of the pinhole lessens.

Figure 22:
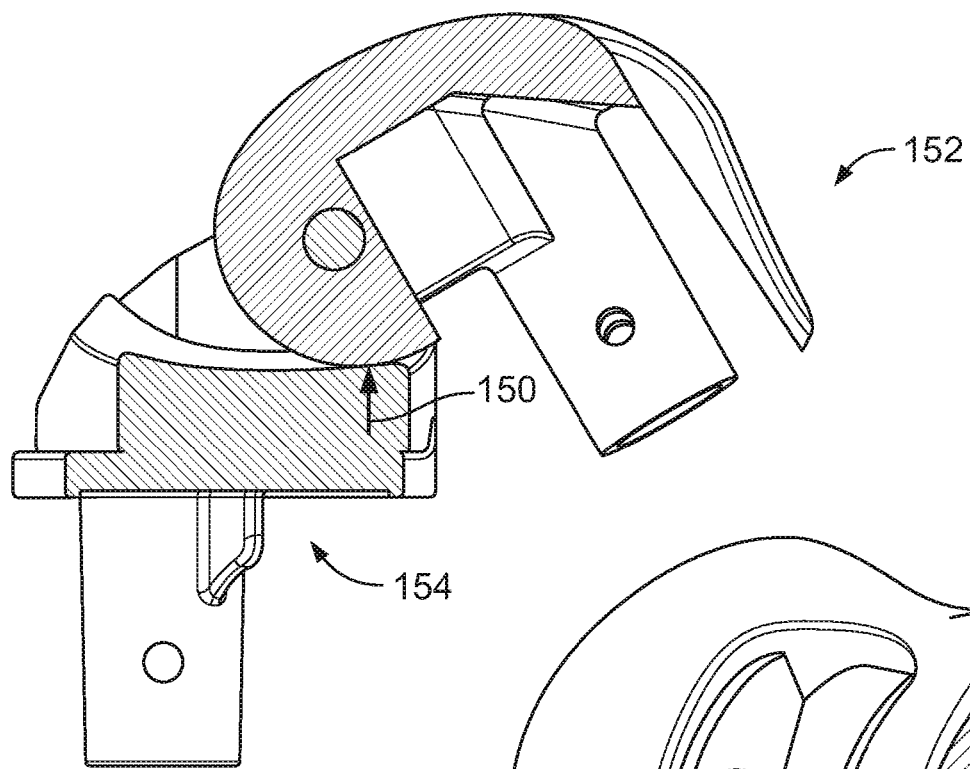
FIGS. 22 and 23 are a side view and an isometric view, respectively, of the hinged knee of FIG. 12 at 150 degrees flexion.
Figure 23:
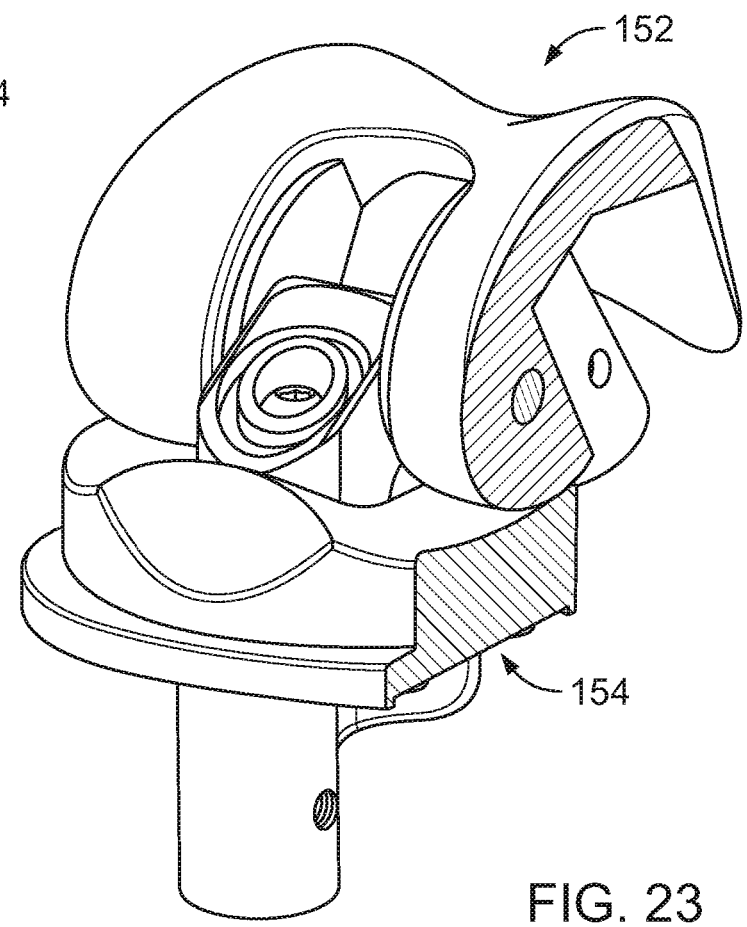

Turning now to FIGS. 22 and 23, FIGS. 22 and 23 are a side view and an isometric view, respectively, of the hinged knee of FIG. 12 at 150 degrees flexion. As the hinged knee continues to rotate, the contact force generally creates A/P translation, and little axial rotation. Again, this is generally consistent with normal knee kinematics. While this embodiment has described A/P translation and axial rotation by surface characteristics of the tibial and femoral components 154 and 152, other embodiments may accomplish these motions in other ways.

The additional embodiments generally try to control lateral forces between the femoral and tibial components. For example, differences in the lateral forces between condyles may create motion. Additionally keeping lateral forces on one side small or zero while controlling the forces on the other side can control axial rotation. For more rotation, forces may be opposite in direction to increase axial rotation. Because rotation is controlled by moments, another method of controlling rotation is to control the moment arms.

Another embodiment may create contact points with corresponding tibial articulation of the femoral articulating surfaces to vary from a plane perpendicular to the transverse axle hinge pin. Generally, the plane would extend through a medial/lateral and/or lateral/medial direction. As the knee moves through the range of motion of the knee, the corresponding insert articulating geometry remains parallel or varies from the same plane creating an axial rotation through whole, in part, and/or various ranges of the range of motion of the joint.

In another embodiment, a concentric sagittal curvature of the medial or lateral femoral condyle's articular surface relative to the transverse hinge pin location and the opposite femoral condyle's articular surface may have eccentric curvature sagittally to the hinge pin location. This shifts the contact with the tibial articulation medial/lateral or lateral/medial at least in part through a range of motion. The tibial articulating surfaces correspond to femoral curvatures and induce axial rotation through whole, in part, and/or various ranges of the range of motion of the joint.

Alternatively, a concentric sagittal curvature of the medial or lateral condyle's articular surface relative to the transverse hinge pin location and the opposite condyle's articular surface having eccentric curvature sagittally to the hinge pin location may create the motion. The tibial articulating surfaces corresponds to femoral curvatures where the corresponding eccentric medial or lateral compartment follows a predetermined path relative to multiple angles of flexion and its corresponding contact points movement. The radial translation of these contact points around the axial rotation around the tibial post/sleeve axis and the corresponding concentric medial or lateral compartment follows a predetermined path relative to multiple angles of flexion and its corresponding contact point's movement around the axial rotation around the tibial post/sleeve axis. This induces an axial rotation through whole, in part, and/or various ranges of the range of motion of the joint.

Another embodiment includes a femoral prosthesis with eccentric sagittal curvature for both of the medial and lateral articulating condylar portions of the femoral prosthesis relative to the transverse axle pin position. A tibial insert with the corresponding articulating geometry, either inclining and/or declining as the eccentric contact points of the femoral articulation translates, shift in a medial/lateral and/or lateral/medial direction to induce an axial rotation through whole, in part, and/or various ranges of the range of motion of the joint.

In another embodiment, a concentric sagittal curvature of the medial or lateral condyle's articular surface relative to the transverse hinge pin location and the opposite condyle's articular surface having eccentric curvature sagittally to the hinge pin location. The tibial articulating surfaces correspond to femoral curvatures where the corresponding eccentric medial or lateral compartment follows a predetermined path relative to multiple angles of flexion and its corresponding contact points movement and the radial translation of these contact points around the axial rotation around the tibial post/sleeve axis. The corresponding concentric medial or lateral compartment follows a predetermined inclining and/or declining path relative to multiple angles of flexion and its corresponding contact points movement around the axial rotation around the tibial post/sleeve axis which induces an axial rotation through whole, in part, and/or various ranges of the range of motion of the joint.

Alternatively, a femoral prosthesis with concentric sagittal curvature for both of the medial and lateral articulating condylar portions of the femoral prosthesis relative to the transverse pin position. A tibial insert with the corresponding articulating geometry, either inclining and/or declining, form an axial rotating path relative to the femoral articulating surfaces. Translational/rotational freedom allows the transverse pin to rotate and translate the femoral prosthesis.

Figure 24:
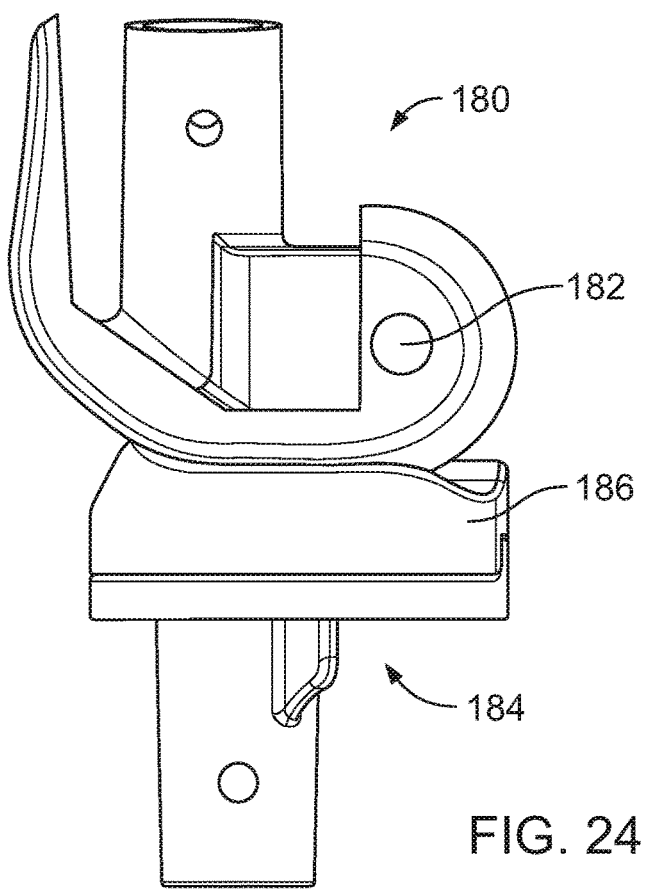
FIGS. 24-26 are a side view, an isometric view, and a top view, respectively, of an embodiment of a hinged knee at extension.
Figure 25:
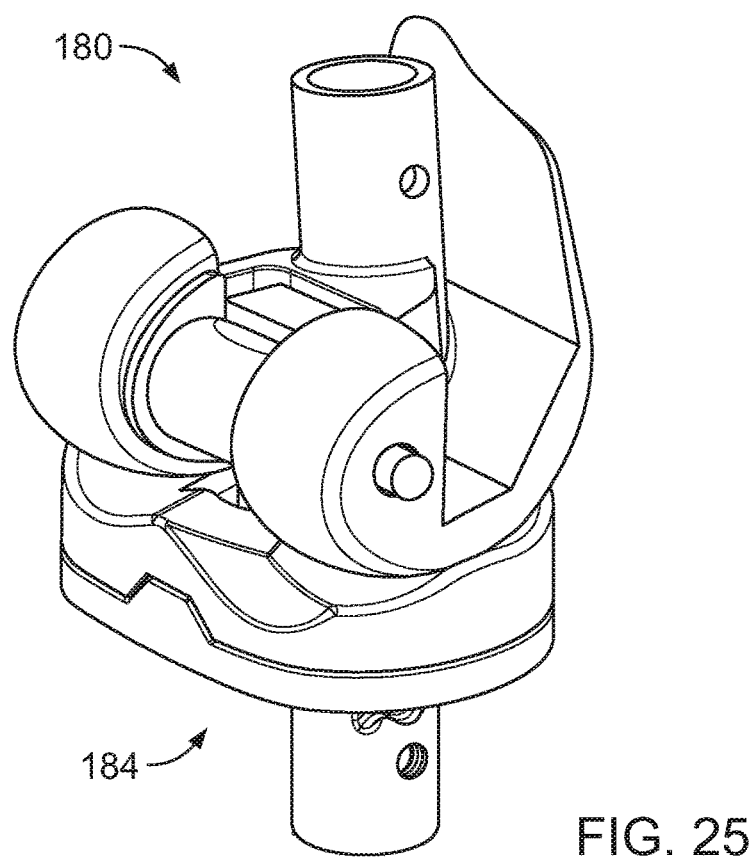
Figure 26:
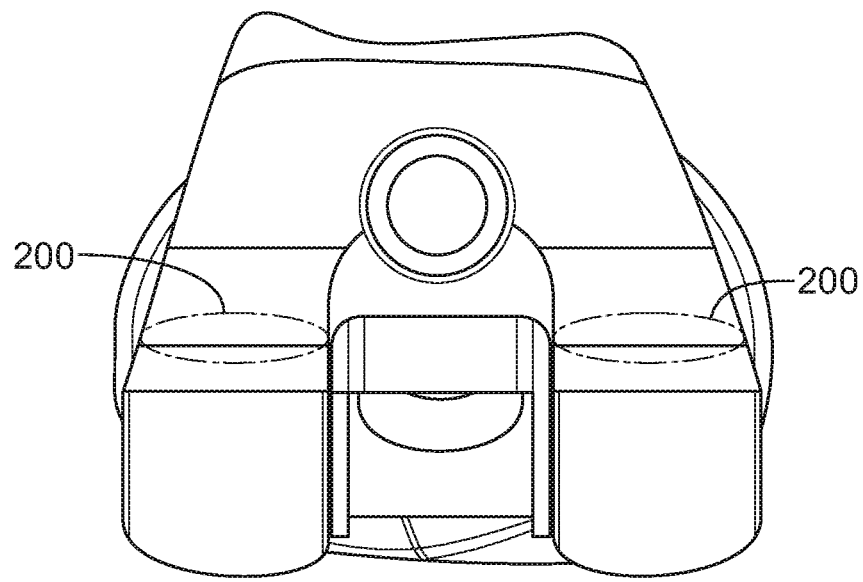

Turning now to FIGS. 24-41, the FIGs. Show side views, isometric views, and top views of an embodiment of a hinged knee in different angles of flexion. FIGS. 24-26 are a side view, an isometric view, and a top view, respectively, of an embodiment of a hinged knee at extension. A femoral component 180 rotates about a pin 182 relative to a tibial component 184. Contact areas 200 show the area in which a tibial insert 186 may contact the femoral component 180. The contact areas 200 in FIGS. 24-41 show how the femoral component 180 rotates and translates along the tibial insert 186.

Figure 27:
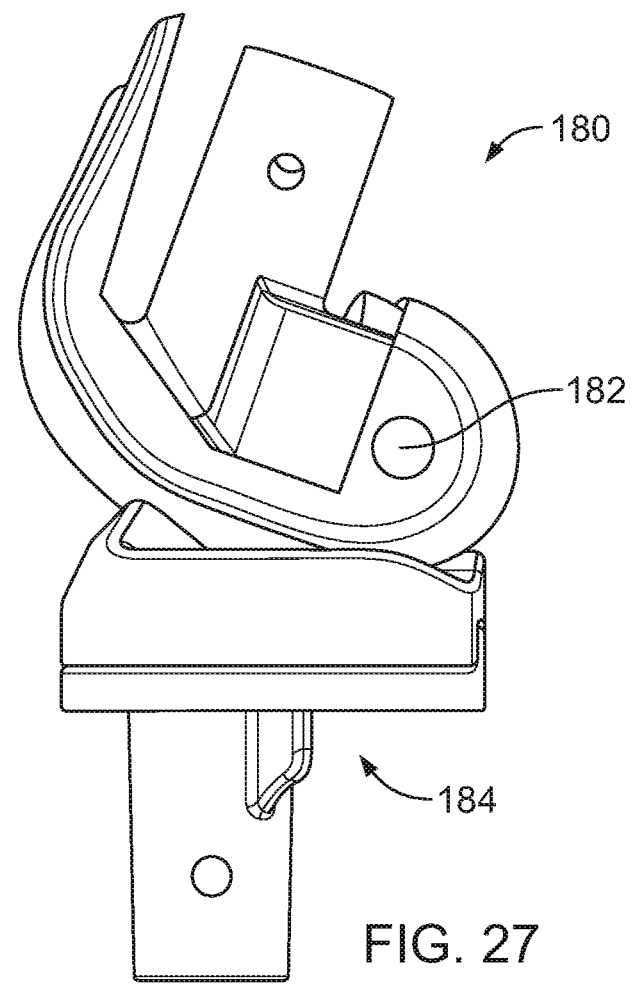
FIGS. 27-29 are a side view, an isometric view, and a top view, respectively, of the hinged knee of FIG. 24 at 20 degrees flexion.
Figure 28:
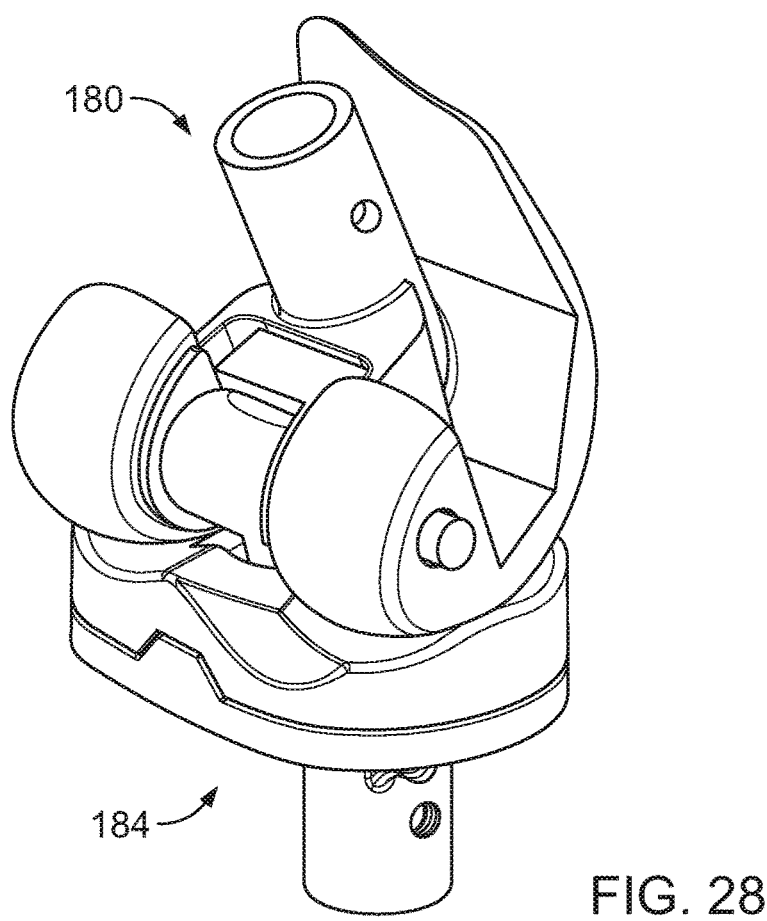
Figure 29:
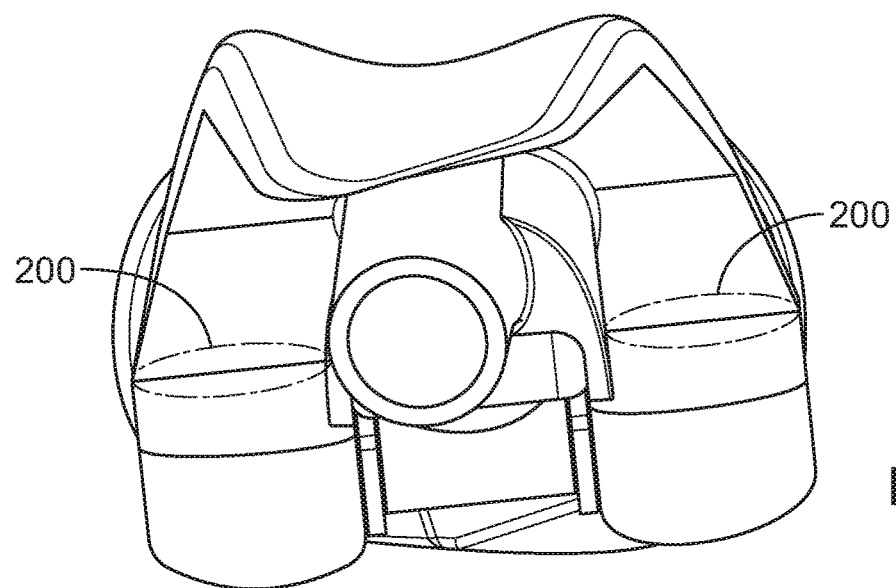

Turning now to FIGS. 27-29, FIGS. 27-29 are a side view, an isometric view, and a top view, respectively, of the hinged knee of FIG. 27 at 20 degrees flexion. The femoral component 180 continues to rotate about the pin 182 relative to the tibial component 184. The contact areas 200, particularly the lateral contact area, have rolled back. The roll back of the lateral contact area corresponds to axial rotation of the femoral component 180 relative to the tibial component 184.

Figure 30:
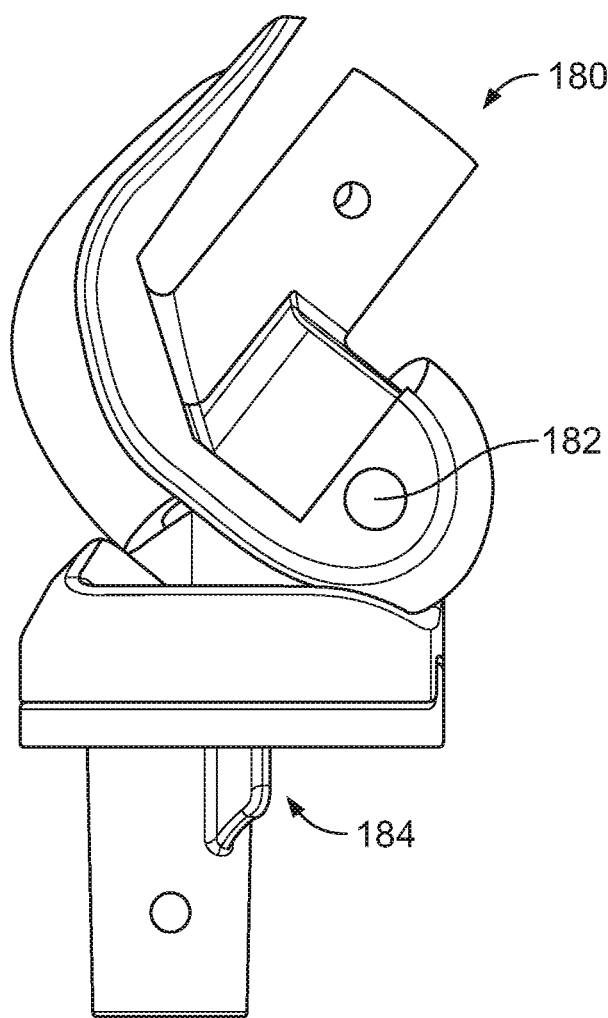
FIGS. 30-32 are a side view, an isometric view, and a top view, respectively, of the hinged knee of FIG. 24 at 40 degrees flexion.
Figure 31:
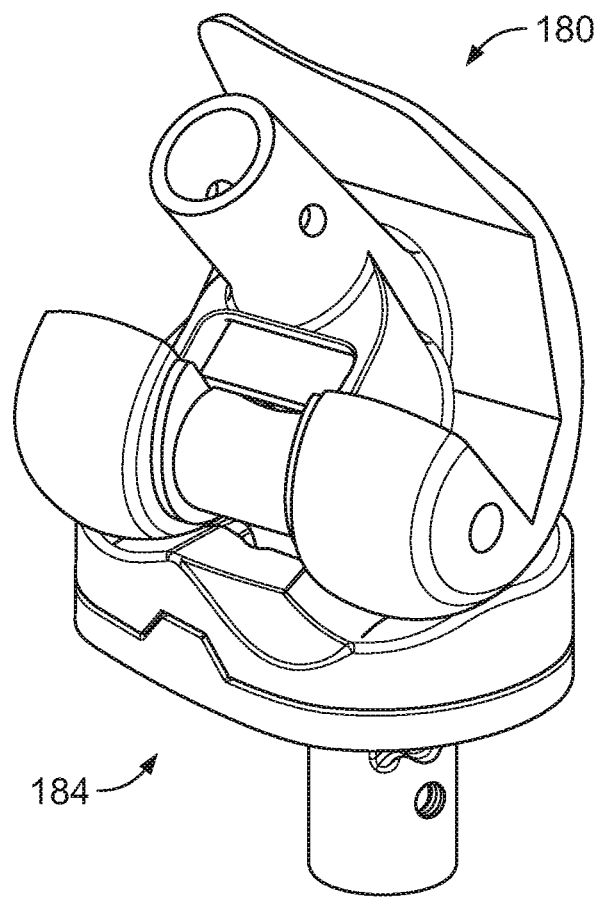
Figure 32:
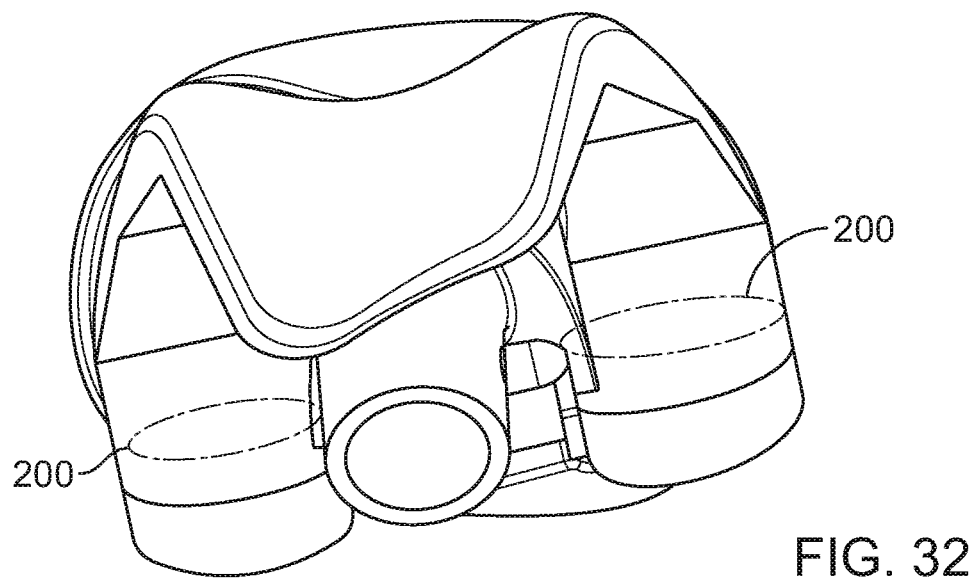

Turning now to FIGS. 30-32, FIGS. 30-32 are a side view, an isometric view, and a top view, respectively, of the hinged knee of FIG. 27 at 40 degrees flexion. The femoral component 180 continues to rotate about the pin 182 relative to the tibial component 184. The contact areas 200 have continued to roll back, and again the lateral contact area has translated farther posteriorly compared to the medial condyle. This corresponds to more axial rotation.

Figure 33:
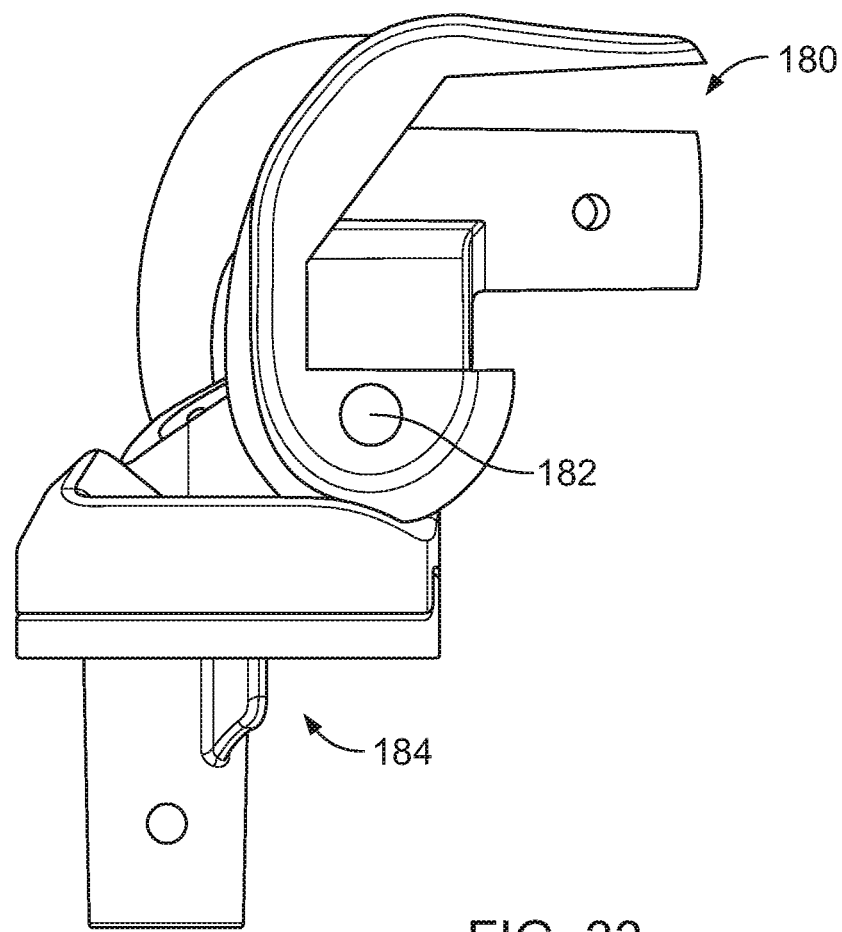
FIGS. 33-35 are a side view, an isometric view, and a top view, respectively, of the hinged knee of FIG. 24 at 90 degrees flexion.
Figure 34:
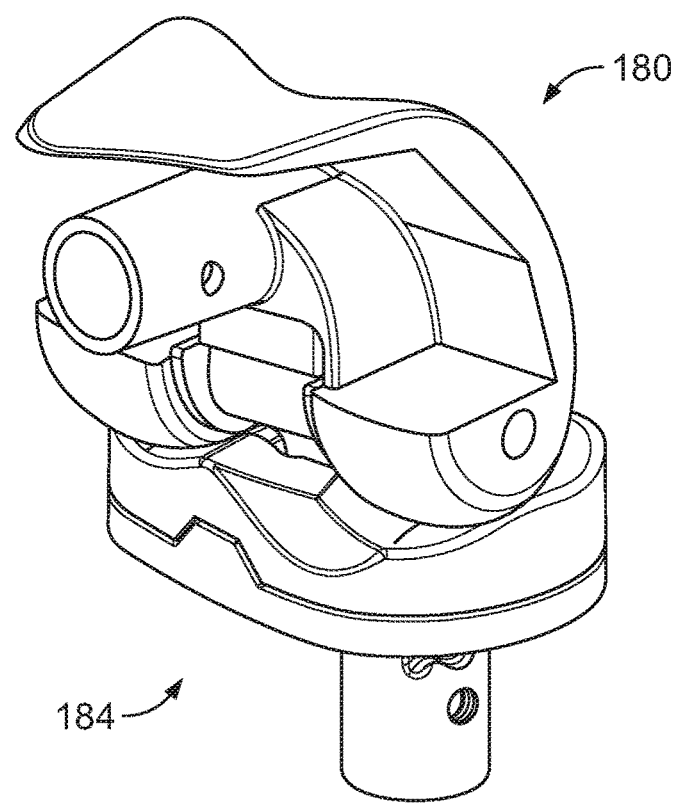
Figure 35:
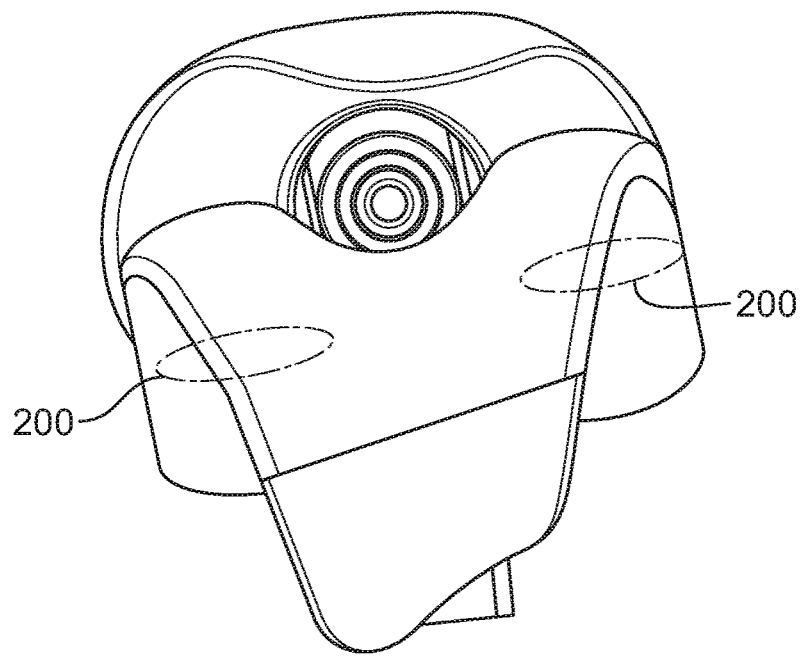

Turning now to FIGS. 33-35, FIGS. 33-35 are a side view, an isometric view, and a top view, respectively, of the hinged knee of FIG. 27 at 90 degrees flexion. The femoral component 180 continues to rotate about the pin 182 relative to the tibial component 184. From 40 degrees to 90 degrees of flexion, the rotation and translation are minimized as the rotation continues through the concentric portion of the curvature.

Figure 36:
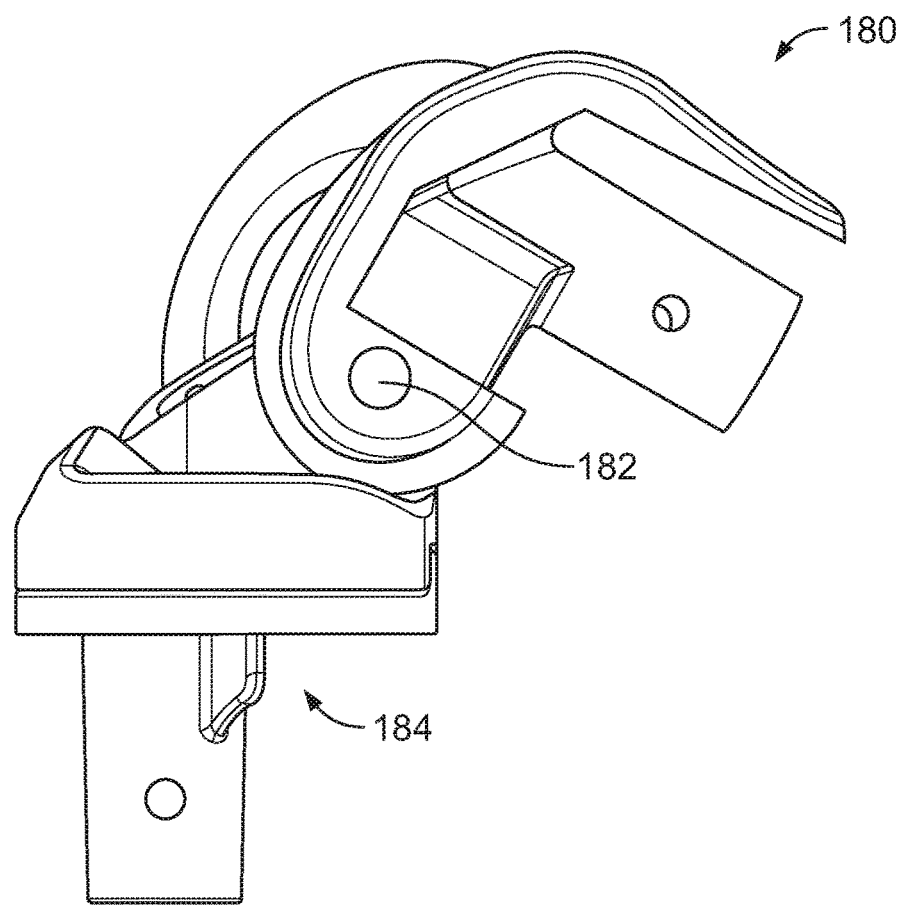
FIGS. 36-38 are a side view, an isometric view, and a top view, respectively, of the hinged knee of FIG. 24 at 120 degrees flexion.
Figure 37:
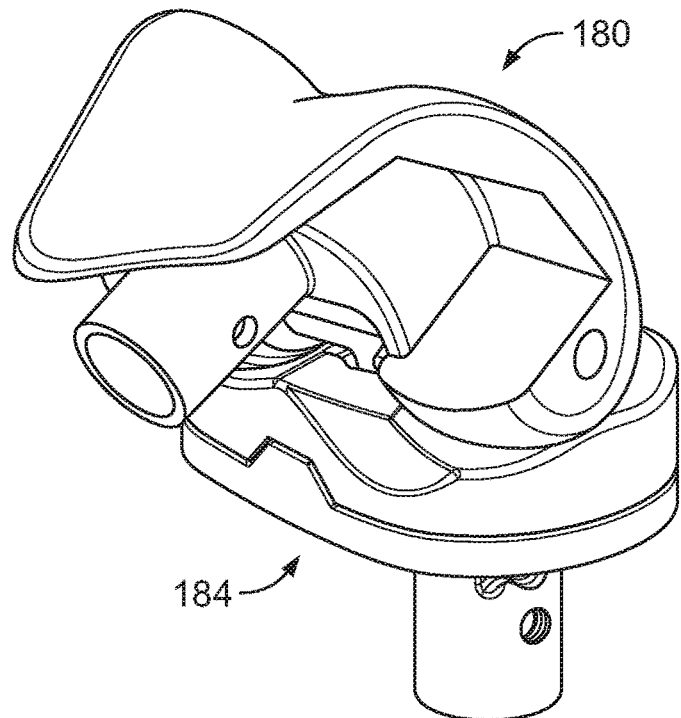
Figure 38:
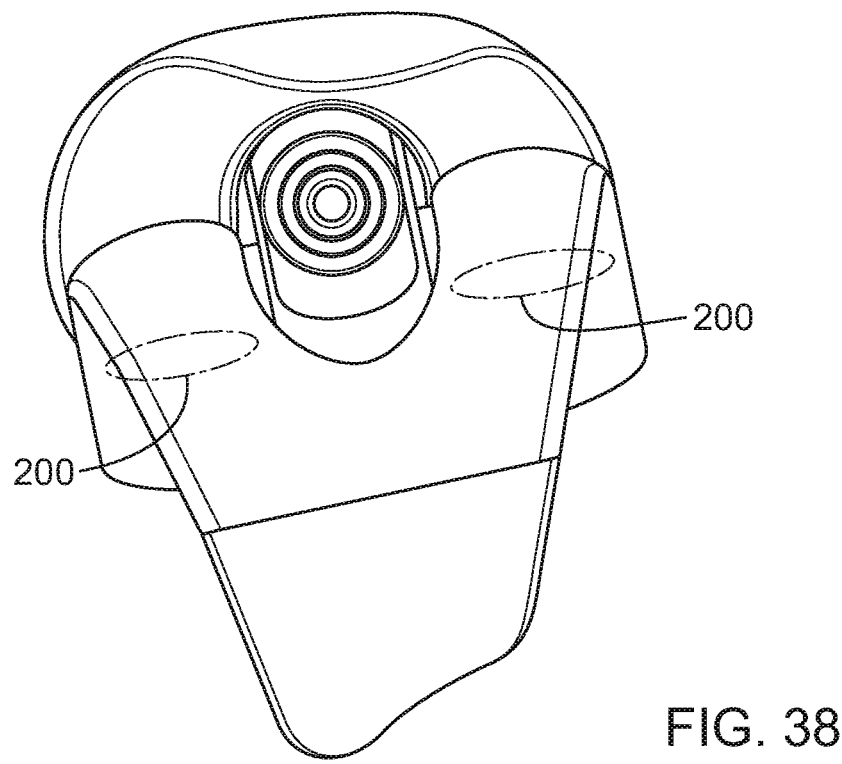

Turning now to FIGS. 36-38, FIGS. 36-38 are a side view, an isometric view, and a top view, respectively, of the hinged knee of FIG. 27 at 120 degrees flexion. The femoral component 180 continues to rotate about the pin 182 relative to the tibial component 184. Similar to the flexion between 40 and 90 degrees, from 90 degrees to 120 degrees of flexion, the rotation and translation are minimized as the rotation continues through the concentric portion of the curvature.

Figure 39:
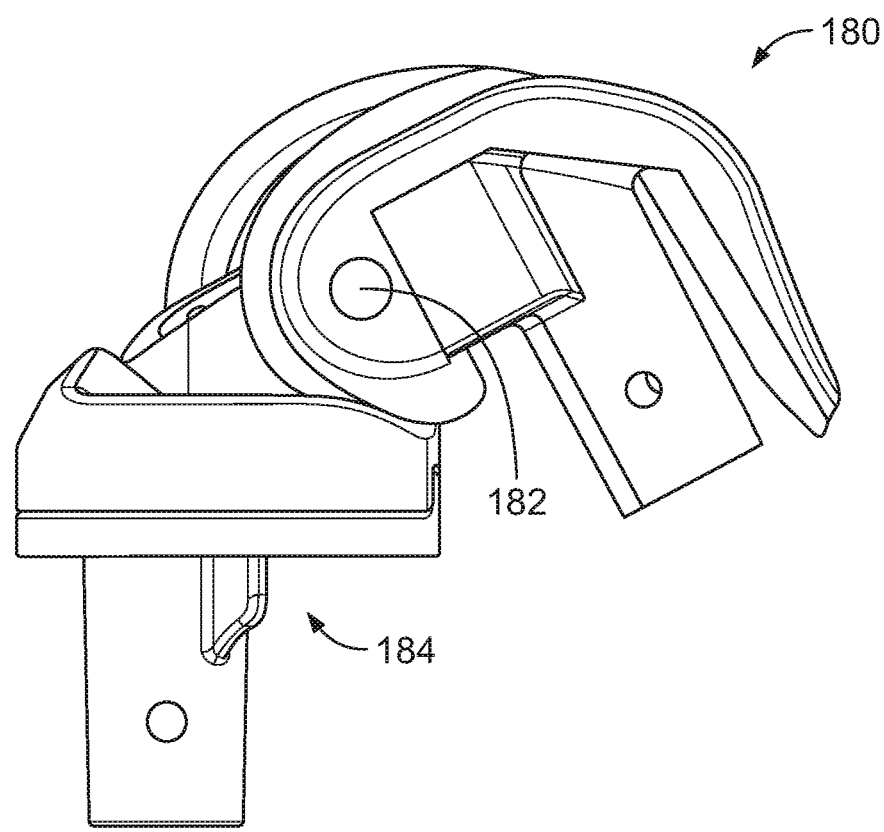
FIGS. 39-41 are a side view, an isometric view, and a top view, respectively, of the hinged knee of FIG. 24 at 150 degrees flexion.
Figure 40:
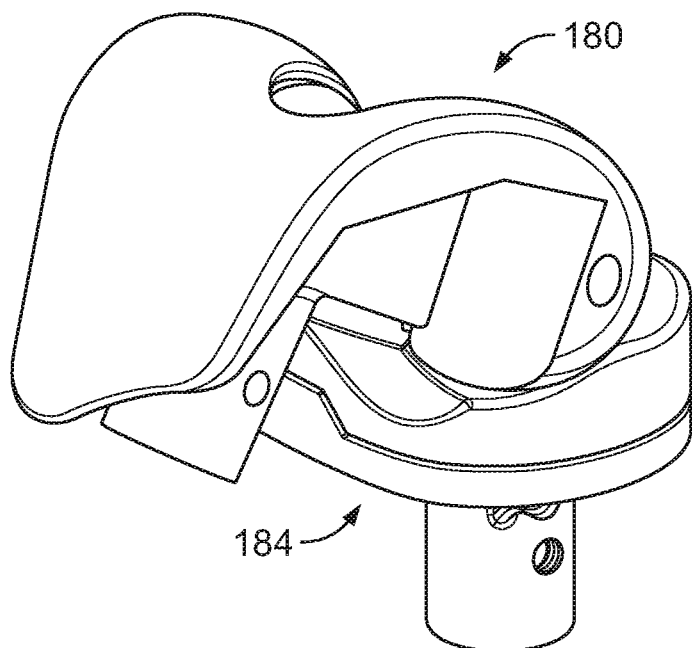
Figure 41:
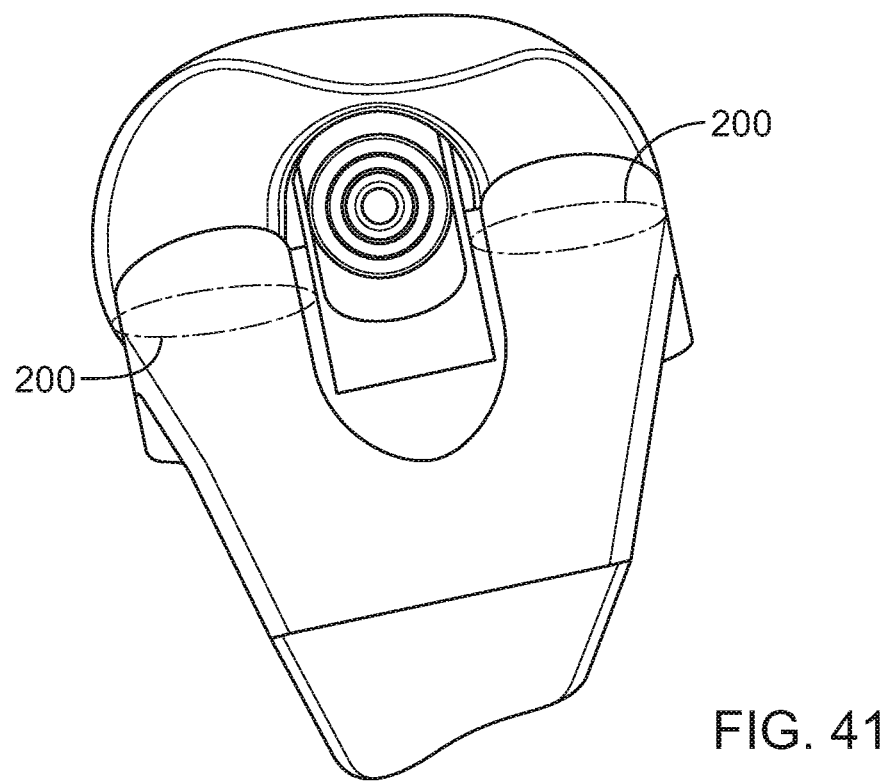

Turning now to FIGS. 39-41, FIGS. 39-41 are a side view, an isometric view, and a top view, respectively, of the hinged knee of FIG. 27 at 150 degrees flexion. The femoral component 180 continues to rotate about the pin 182 relative to the tibial component 184. As the flexion continues from 120 to 150 degrees, the contact areas 200 translate and have little axial rotation.

Thus, as the knee flexes, the rotation allows for the patella to slide along the patellar groove without generating forces in the patella. Additionally, with movement approximating the natural movement, the hinged knee does not generate forces in the soft tissue. This may help preserve soft tissue that is initially damaged by surgery. Moreover, some soft tissue is removed during surgery, and thus the remaining soft tissue must work harder to complete tasks. Reducing the forces on soft tissue can reduce swelling, pain and additional stresses on the soft tissue after surgery.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A knee prosthesis, comprising:
   a tibial component arranged and configured to attach to a patient's tibia, the tibial component having a bearing surface;
   a femoral component arranged and configured to couple to the tibial component so that, in use, the femoral component rotates relative to the tibial component and the femoral component translates in an anterior/posterior (A/P) direction relative to the tibial component, the femoral component comprising:
      a medial condyle; and
      a lateral condyle;
      wherein the medial and lateral condyles each have a curved surface arranged and configured to contact the bearing surface of the tibial component to induce rotation and translation of the femoral component relative to the tibial component; and
   a connecting member including a pin for coupling the femoral component to the tibial component, the connecting member including a rotational axis and an opening to receive an elongated member associated with the tibial component; the pin being arranged and configured to axially rotate and axially translate in the A/P direction to enable rotation and translation of the femoral component relative to the tibial component.

2. The knee prosthesis of claim 1, wherein the connecting member further comprises a sleeve having a pin opening, the pin being positioned within the pin opening of the sleeve, the pin being arranged and configured to axially translate relative to the sleeve to induce rotation and translation of the femoral component relative to the tibial component.

3. The knee prosthesis of claim 2, wherein the pin couples the medial condyle and the lateral condyle to the sleeve, the sleeve includes the opening to receive the elongated member associated with the tibial component to couple the femoral component to the tibial component.

4. The knee prosthesis of claim 2, wherein the femoral component is arranged and configured to rotate about the pin and the sleeve.

5. The knee prosthesis of claim 2, wherein the curved surfaces of the medial and lateral condyles are arranged and configured with a center of rotation positioned outside the pin.

6. The knee prosthesis of claim 2, wherein the elongated member comprises a post arranged and configured to be received within the opening of the sleeve for coupling the sleeve to the tibial component.

7. The knee prosthesis of claim 2, wherein the elongated member comprises a post extending from the tibial component.

8. The knee prosthesis of claim 7, wherein the post is asymmetrically positioned relative to the tibial component.

9. The knee prosthesis of claim 7, further comprising a post sleeve for coupling the post to the sleeve.

10. The knee prosthesis of claim 9, wherein the post sleeve is arranged and configured to rotate and translate relative to the post.

11. The knee prosthesis of claim 10, wherein the pin is arranged and configured to rotate and translate relative to the post and the post sleeve.

12. The knee prosthesis of claim 2, wherein the pin is positioned posteriorly relative to a center of the knee prosthesis.

13. The knee prosthesis of claim 2, wherein the curved surfaces of the medial and lateral condyles are eccentric with respect to a center of rotation of the femoral component.

14. The knee prosthesis of claim 1, wherein the curved surfaces of the medial and lateral condyles are arranged and configured to be eccentric with respect to a center of rotation of the pin.

15. The knee prosthesis of claim 1, wherein the curved surfaces of the medial and lateral condyles each include a first distal portion having a first center of rotation, a second posterior portion having a second center of rotation, and a third proximal portion having a third center of rotation, wherein the first and third centers of rotation are eccentric to the pin, the second center of rotation is concentric with the pin.

16. The knee prosthesis of claim 1, wherein the tibial component comprises a tibial insert and a tibial base, the tibial insert including the bearing surface.

17. The knee prosthesis of claim 16, wherein the tibial insert includes a post hole for receiving the elongated member associated with the tibial component.

18. The knee prosthesis of claim 16, wherein a posterior portion of the tibial insert slopes to rotate and translate the femoral component posteriorly.

19. A knee prosthesis, comprising:
a tibial component arranged and configured to attach to a patient's tibia, the tibial component including a tibial base and a tibial insert, the tibial insert having a bearing surface;
a femoral component arranged and configured to couple to the tibial component so that, in use, the femoral component rotates relative to the tibial component and the femoral component translates in an anterior/posterior (A/P) direction relative to the tibial component, the femoral component comprising:
a medial condyle; and
a lateral condyle;
wherein the medial and lateral condyles each have a curved surface arranged and configured to contact the bearing surface of the tibial insert to induce rotation and translation of the femoral component relative to the tibial component; and
a connecting member for coupling the femoral component to the tibial component, the connecting member including:
a pin; and
a sleeve having a pin opening and a post opening, the pin being positioned within the pin opening of the sleeve, an elongated member associated with the tibial component being positioned within the post opening for coupling the femoral component to the tibial component;
wherein the curved surfaces of the medial and lateral condyles each include a first distal portion having a first center of rotation, a second posterior portion having a second center of rotation, and a third proximal portion having a third center of rotation, wherein the first and third centers of rotation are eccentric to the pin, the second center of rotation is concentric with the pin; and
wherein the pin is arranged and configured to translate relative to the sleeve and the positioning of the first, second, and third centers of rotation relative to the pin enable the femoral component to axially rotate and axially translate in the A/P direction relative to the tibial component.

* * * * *